US010365253B2

United States Patent
Nagai et al.

(10) Patent No.: US 10,365,253 B2
(45) Date of Patent: Jul. 30, 2019

(54) METHOD FOR MANUFACTURING OUTER JOINT MEMBER FOR CONSTANT VELOCITY UNIVERSAL JOINT AND ULTRASONIC FLAW DETECTION METHOD FOR WELDED SECTION

(71) Applicant: NTN Corporation, Osaka (JP)

(72) Inventors: Hiromi Nagai, Shizuoka (JP); Yasuhiko Sakakibara, Shizuoka (JP)

(73) Assignee: NTN CORPORATION, Osaka (JP)

( * ) Notice: Subject to any disclaimer, the term of this patent is extended or adjusted under 35 U.S.C. 154(b) by 0 days.

(21) Appl. No.: 15/741,793

(22) PCT Filed: Jun. 10, 2016

(86) PCT No.: PCT/JP2016/067357
§ 371 (c)(1),
(2) Date: Jan. 4, 2018

(87) PCT Pub. No.: WO2017/006702
PCT Pub. Date: Jan. 12, 2017

(65) Prior Publication Data
US 2018/0193942 A1     Jul. 12, 2018

(30) Foreign Application Priority Data

Jul. 9, 2015   (JP) ................................. 2015-137941

(51) Int. Cl.
*F16D 3/20*      (2006.01)
*B23K 15/00*    (2006.01)
(Continued)

(52) U.S. Cl.
CPC ........... *G01N 29/275* (2013.01); *B23K 15/00* (2013.01); *B23K 15/0006* (2013.01);
(Continued)

(58) Field of Classification Search
CPC .. F16D 2250/0076; F16D 1/068; F16D 1/027; G01N 2291/267–2677;
(Continued)

(56) References Cited

U.S. PATENT DOCUMENTS 4,065,960 A * 1/1978 Grabendorfer ........ G01N 29/11
 73/609
4,270,389 A * 6/1981 Shiraiwa ................ G01N 29/38
 73/1.82
(Continued)

FOREIGN PATENT DOCUMENTS

JP       56142455 A   * 11/1981   ......... G01N 29/0618
JP       58-144742         8/1983
(Continued)

OTHER PUBLICATIONS

King, History of the Lathe (Year: 2008).*
(Continued)

*Primary Examiner* — Justin Seo
*Assistant Examiner* — David L Singer
(74) *Attorney, Agent, or Firm* — Wenderoth, Lind & Ponack, L.L.P.

(57) ABSTRACT

A manufacturing method is used for an outer joint member of a constant velocity universal joint. The outer joint member includes a cup section having track grooves formed in an inner periphery of the cup section, which are engageable with torque transmitting elements, and a shaft section formed at a bottom portion of the cup section. The outer joint member is constructed by forming the cup section and the shaft section as separate members, and by welding a cup member forming the cup section and a shaft member forming the shaft section to each other. The manufacturing method at least includes welding the cup member and the shaft member by irradiating a beam to joining end portions
(Continued)

of the cup member and the shaft member, and inspecting a welded portion formed in the welding by a plurality of ultrasonic flaw detection methods with one probe.

7 Claims, 23 Drawing Sheets

(51) Int. Cl.
| | |
|---|---|
| *B23K 26/21* | (2014.01) |
| *B23K 31/00* | (2006.01) |
| *B23K 31/12* | (2006.01) |
| *F16D 1/027* | (2006.01) |
| *G01N 29/04* | (2006.01) |
| *G01N 29/22* | (2006.01) |
| *G01N 29/28* | (2006.01) |
| *G01N 29/275* | (2006.01) |
| *G01N 29/265* | (2006.01) |
| *B21K 1/76* | (2006.01) |

(52) U.S. Cl.
CPC .......... *B23K 15/0053* (2013.01); *B23K 26/21* (2015.10); *B23K 31/00* (2013.01); *B23K 31/125* (2013.01); *F16D 1/027* (2013.01); *F16D 3/20* (2013.01); *G01N 29/043* (2013.01); *G01N 29/221* (2013.01); *G01N 29/265* (2013.01); *B21K 1/765* (2013.01); *F16D 2250/0076* (2013.01); *G01N 29/28* (2013.01); *G01N 2291/0234* (2013.01); *G01N 2291/044* (2013.01); *G01N 2291/2634* (2013.01); *G01N 2291/2675* (2013.01)

(58) Field of Classification Search
CPC ... G01N 2291/2634; G01N 2291/0234; G01N 29/275; G01N 29/225; G01N 29/4445; G01N 29/28; G01N 29/043; G01N 29/221; G01N 2291/044; G01N 2291/0289; B21K 1/765; B23K 15/0006; B23K 31/125; F16C 3/023; G05B 19/4183; G05B 19/41875
USPC ..................... 73/622, 588; 228/104; 700/110
See application file for complete search history.

(56) References Cited

U.S. PATENT DOCUMENTS

| | | | | |
|---|---|---|---|---|
| 4,406,167 A | * | 9/1983 | Maeda ................... | G01N 29/11 73/622 |
| 4,586,379 A | * | 5/1986 | Burkhardt, Jr. ....... | G01N 29/265 73/622 |
| 5,108,693 A | * | 4/1992 | Landry .................. | G01N 29/11 376/245 |
| 5,681,996 A | * | 10/1997 | White .................. | G01N 29/043 73/622 |
| 2002/0013635 A1 | * | 1/2002 | Gotou .................. | G01M 13/045 700/108 |
| 2006/0048576 A1 | * | 3/2006 | Kiuchi .................... | F16C 33/12 73/593 |
| 2006/0288756 A1 | * | 12/2006 | De Meurechy ...... | G01N 17/006 73/1.01 |
| 2008/0210009 A1 | | 9/2008 | Tanishiki | |
| 2009/0095087 A1 | * | 4/2009 | Yamano ............... | G01N 29/043 73/622 |
| 2009/0216360 A1 | * | 8/2009 | Ikeda ........................ | F16C 3/02 700/110 |
| 2013/0218490 A1 | * | 8/2013 | Poirier ................. | G01N 29/069 702/56 |
| 2014/0115857 A1 | * | 5/2014 | Hatano ................. | B23P 19/086 29/407.1 |
| 2014/0291301 A1 | * | 10/2014 | Tosaji ..................... | F16C 3/023 219/121.14 |
| 2017/0234836 A1 | * | 8/2017 | Nagai .................. | G01N 29/275 73/627 |
| 2018/0259003 A1 | * | 9/2018 | Nagai .................... | G01N 29/27 |

FOREIGN PATENT DOCUMENTS

| | | | | | |
|---|---|---|---|---|---|
| JP | 06102258 | A | * | 4/1994 | |
| JP | 8-110332 | | | 4/1996 | |
| JP | 10-19859 | | | 1/1998 | |
| JP | 2001-50941 | | | 2/2001 | |
| JP | 2006-220608 | | | 8/2006 | |
| JP | 2009-103210 | | | 5/2009 | |
| JP | 2012229714 | A | * | 11/2012 | |
| JP | 2013-100859 | | | 5/2013 | |
| JP | 2013156104 | A | * | 8/2013 | |
| JP | 2015-064101 | | | 4/2015 | |
| WO | WO-03060507 | A1 | * | 7/2003 | ............. F16C 33/12 |
| WO | WO-2012032926 | A1 | * | 3/2012 | ........... B23K 20/129 |
| WO | WO-2013069433 | A1 | * | 5/2013 | ............. F16C 3/023 |

OTHER PUBLICATIONS

Massachusetts Institute of Technology, machine shop training: Lathe (Year: 2010).*
International Search Report dated Sep. 6, 2016 in International (PCT) Application No. PCT/JP2016/067357.
International Preliminary Report on Patentability and Written Opinion of the International Searching Authority dated Jan. 9, 2018 in International (PCT) Application No. PCT/JP2016/067357.
Extended European Search Report dated Mar. 7, 2019 in corresponding European Patent Application No. 16821172.0.

* cited by examiner

METHOD FOR MANUFACTURING OUTER JOINT MEMBER FOR CONSTANT VELOCITY UNIVERSAL JOINT AND ULTRASONIC FLAW DETECTION METHOD FOR WELDED SECTION

TECHNICAL FIELD

The present invention relates to a manufacturing method for an outer joint member of a constant velocity universal joint, and to an ultrasonic flaw detection-inspection method for a welded portion.

BACKGROUND ART

In a constant velocity universal joint, which is used to construct a power transmission system for automobiles and various industrial machines, two shafts on a driving side and a driven side are coupled to each other to allow torque transmission therebetween, and rotational torque can be transmitted at a constant velocity even when the two shafts form an operating angle. The constant velocity universal joint is roughly classified into a fixed type constant velocity universal joint that allows only angular displacement, and a plunging type constant velocity universal joint that allows both the angular displacement and axial displacement. In a drive shaft configured to transmit power from an engine of an automobile to a driving wheel, for example, the plunging type constant velocity universal joint is used on a differential side (inboard side), and the fixed type constant velocity universal joint is used on a driving wheel side (outboard side).

Irrespective of the plunging type and the fixed type, the constant velocity universal joint mainly includes an outer joint member including a cup section having track grooves formed in an inner peripheral surface thereof and engageable with torque transmitting elements, and a shaft section that extends from a bottom portion of the cup section in an axial direction. In many cases, the outer joint member is constructed by integrally forming the cup section and the shaft section by subjecting a rod-like solid blank (bar material) to plastic working such as forging and ironing or processing such as cutting work, heat treatment, and grinding.

Incidentally, as the outer joint member, an outer joint member including a long shaft section (long stem) may sometimes be used. In order to equalize lengths of a right intermediate shaft and a left intermediate shaft, the long stem is used for an outer joint member on the inboard side that corresponds to one side of the drive shaft. The long stem is rotatably supported by a rolling bearing. Although varied depending on vehicle types, the length of the long stem section is approximately from 300 mm to 400 mm in general. In the outer joint member, the long shaft section causes difficulty in integrally forming the cup section and the shaft section with high accuracy. Therefore, there has been proposed an outer joint member that is constructed by forming the cup section and the shaft section as separate members and applying electron beam welding (Patent Document 1).

Defects such as blowholes and solidification cracks may occur in the welded portion. Thus, a quality check by an ultrasonic flaw detection method is generally performed. The ultrasonic flaw detection method has a problem in that detection accuracy is degraded by limitation of a product shape and orientation of defects. In addition, there is a case in which a non-inspectable region (hereinafter also referred to as "dead zone") specific to a shape of a workpiece is present depending on a method of irradiation, which results in limitation of an inspection range. In order to prevent degradation in detection accuracy, there has been proposed a method of irradiating ultrasonic waves from a plurality of different directions to secure the detection accuracy and the detection range (Patent Document 2).

PRIOR ART DOCUMENTS

Patent Documents

Patent Document 1: JP 2015-64101 A
Patent Document 2: JP 58-144742 A

SUMMARY OF THE INVENTION

Problems to be the Invention

According to the manufacturing method for an outer joint member described in Patent Literature 1, a joining end surface of the cup member and a joining end surface of the shaft member are brought into abutment against each other, and the cup member and the shaft member are welded by irradiating a beam from an outer side to the abutment portion in a radial direction. Further, an outer diameter of the joining end surface is set to an equal dimension for each joint size. With this configuration, there has been proposed an excellent manufacturing method for an outer joint member, which is capable of increasing the strength of the welded portion and the quality, reducing the welding cost, enhancing productivity of the cup member and the shaft member, achieving the cost reduction through the standardization of a product type of the cup member, and reduction of the burden of production management. However, no focus is given to improvement in inspection accuracy and ease of inspection for the welded portion.

The ultrasonic flaw detection device described in Patent Literature 2 includes two or more fixed probes to irradiate ultrasonic waves from a plurality of different directions, and the inspection is performed while conveying a workpiece by, for example, a conveyer in many cases. Further, there is difficulty in application to a product having a complicated shape. For example, for joining of a cylindrical component such as an outer joint member of a constant velocity universal joint having an outer diameter of $\varphi 100$ mm or less, detection of a defect of about 0.5 mm is required for an entire region. The inspection range for each workpiece is small. Therefore, with the ultrasonic flaw detection device including the above-mentioned conveyance device, the size of the facility is increased, with the result that the equipment cost becomes more expensive. Further, products have different shapes. Therefore, there is difficulty in application of a simple adjustment mechanism described in Patent Literature 2, with the result that labor is required for adjustment of setups. Thus, it has been found that the above-mentioned technology is not applicable at the level of enabling industrial production of an outer joint member of a constant velocity universal joint being a mass-produced product for automobiles and the like.

The present invention has been proposed in view of the above-mentioned problems, and has an object to provide a manufacturing method for an outer joint member, which enables defect detection for a welded portion of an outer joint member of a constant velocity universal joint being a mass-produced product for automobiles and the like with high detection accuracy and in a wide detection range and also at the level of enabling industrial production, thereby being capable of increasing the strength of the welded portion and the quality, enhancing productivity, and achieving reduction of the manufacturing cost.

Solution to the Problems

As a result of various studies conducted to achieve the above-mentioned object, the inventors of the present invention have arrived at the present invention with new idea of performing inspection by a plurality of ultrasonic flaw detection methods with one probe to secure the high detection accuracy and the wide detection range.

As a technical measure to achieve the above-mentioned object, according to one embodiment of the present invention, there is provided a manufacturing method for an outer joint member of a constant velocity universal joint, the outer joint member comprising: a cup section having track grooves formed in an inner periphery of the cup section, which are engageable with torque transmitting elements; a shaft section formed at a bottom portion of the cup section, the outer joint member being constructed by forming the cup section and the shaft section as separate members, and by welding a cup member forming the cup section and a shaft member forming the shaft section to each other, the manufacturing method at least comprising: a welding step of welding the cup member and the shaft member by irradiating a beam to joining end portions of the cup member and the shaft member; and an ultrasonic flaw detection-inspection step of inspecting a welded portion formed in the welding step by a plurality of ultrasonic flaw detection methods with one probe.

Further, according to one embodiment of the present invention, there is provided an ultrasonic flaw detection-inspection method for a welded portion of an outer joint member of a constant velocity universal joint, the outer joint member comprising: a cup section having track grooves formed in an inner periphery of the cup section, which are engageable with torque transmitting elements; and a shaft section formed at a bottom portion of the cup section, the outer joint member being constructed by forming the cup section and the shaft section as separate members, and by welding a cup member forming the cup section and a shaft member forming the shaft section to each other, the ultrasonic flaw detection inspection method comprising inspecting the welded portion by a plurality of ultrasonic flaw detection methods with one probe.

The above-mentioned configuration enables achievement of a manufacturing method for an outer joint member, which enables defect detection for a welded portion of an outer joint member of a constant velocity universal joint being a mass-produced product for automobiles and the like with high detection accuracy and in a wide detection range and also at the level of enabling industrial production, thereby being capable of increasing the strength of the welded portion and the quality, enhancing productivity, and achieving reduction of the manufacturing cost.

A position and an angle of the above-mentioned probe are freely controlled. Therefore, a plurality of (two or more) different flaw detection methods such as a normal beam method and an angled beam method can be performed with one probe, thereby being capable of preventing degradation in detection accuracy due to orientation of a defect and preventing reduction in detection range due to presence of the dead zone.

It is preferred that the position and the angle of the above-mentioned probe be controlled by a program. In this case, the manufacturing method is applicable to a complicated workpiece (outer joint member) shape and an outer joint member assigned with a different product number. At the same time, adjustment of setups for equipment can easily be performed, thereby being capable of securing repeatability of inspection.

In the above-mentioned ultrasonic flaw detection-inspection step, a workpiece formed by welding the cup member and the shaft member is rotated during inspection, thereby being capable of performing inspection for one rotation (360°) of the welded portion in a short period of time.

Effects of the Invention

With the manufacturing method for an outer joint member of a constant velocity universal joint and the ultrasonic flaw detection-inspection method for a welded portion according to the present invention, it is possible to achieve the manufacturing method for an outer joint member, which enables defect detection for a welded portion of an outer joint member of a constant velocity universal joint being a mass-produced product for automobiles and the like with high detection accuracy and in a wide detection range and also at the level of enabling industrial production, thereby being capable of increasing the strength of the welded portion and the quality, enhancing productivity, and achieving reduction of the manufacturing cost.

BRIEF DESCRIPTION OF DRAWINGS

FIG. 2a is an enlarged partial vertical sectional view for illustrating the outer joint member of FIG. 1.

FIG. 2b is an enlarged view of the portion A of FIG. 2a.

FIG. 2c is an enlarged view for illustrating a shape of the portion A of FIG. 2a before welding.

EMBODIMENTS OF THE INVENTION

Now, description is made of embodiments of the present invention with reference to the drawings.

Figure 1:
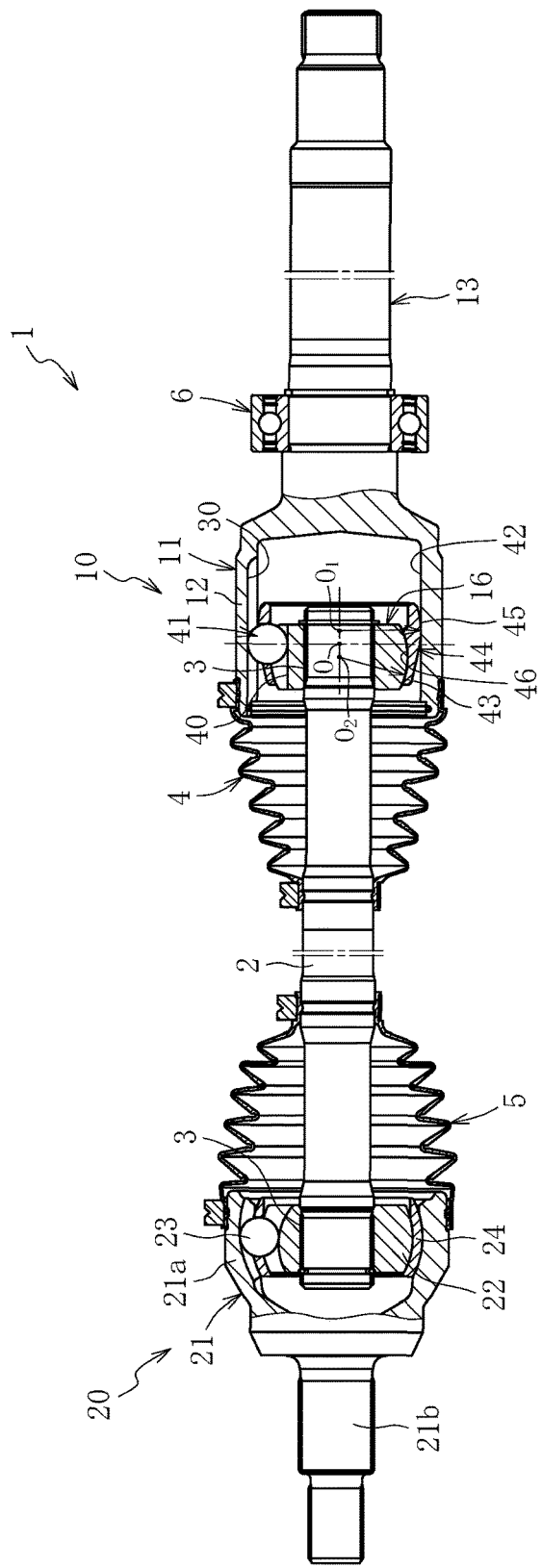
FIG. 1 is a view for illustrating the entire structure of a drive shaft using an outer joint member manufactured based on a manufacturing method according to a first embodiment of the present invention.
Figure 2:
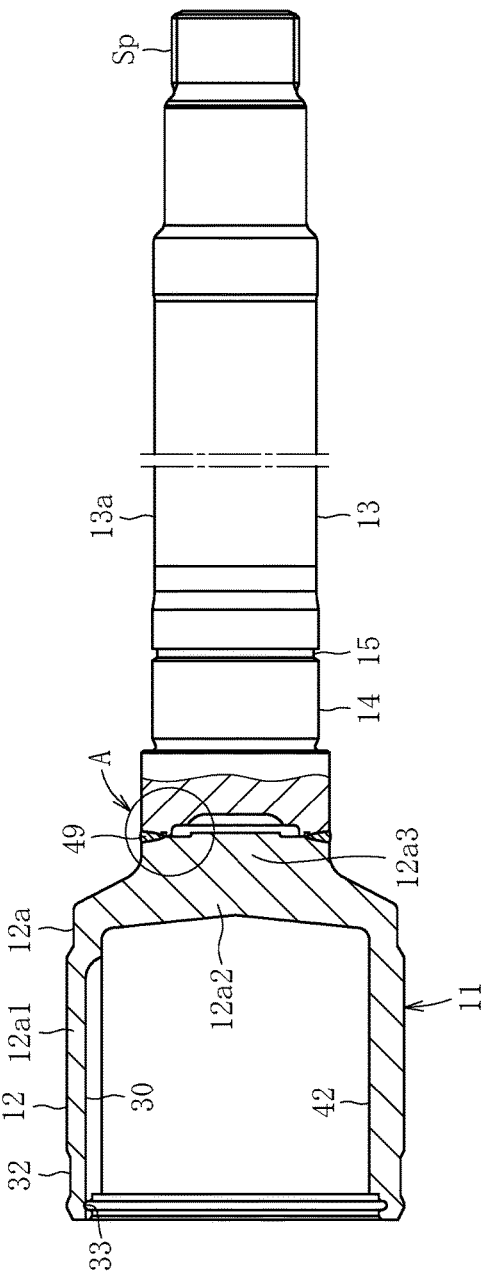

A manufacturing method for an outer joint member of a constant velocity universal joint according to a first embodiment of the present invention is illustrated in FIG. 3 to FIG. 22. An outer joint member which is manufactured based on the manufacturing method according to the first embodiment and a constant velocity universal joint are illustrated in FIG. 1 and FIG. 2. First, the outer joint member and the constant velocity universal joint are described with reference to FIG. 1 and FIG. 2, and subsequently, the manufacturing method for an outer joint member according to the first embodiment is described with reference to FIG. 3 to FIG. 22.

FIG. 1 is a view for illustrating the entire structure of a drive shaft 1 using an outer joint member 11 manufactured based on the manufacturing method according to the first embodiment. The drive shaft 1 mainly comprises a plunging type constant velocity universal joint 10 arranged on a differential side (right side of FIG. 1: hereinafter also referred to as "inboard side"), a fixed type constant velocity universal joint 20 arranged on a driving wheel side (left side of FIG. 1: hereinafter also referred to as "outboard side"), and an intermediate shaft 2 configured to couple both the constant velocity universal joints 10 and 20 to each other to allow torque transmission therebetween.

The plunging type constant velocity universal joint 10 illustrated in FIG. 1 is a so-called double-offset type constant velocity universal joint (DOJ). The constant velocity universal joint 10 comprises the outer joint member 11 comprising a cup section 12 and a long shaft section (hereinafter referred to also as "long stem section") 13 that extends from a bottom portion of the cup section 12 in an axial direction, an inner joint member 16 housed along an inner periphery of the cup section 12 of the outer joint member 11, balls 41 serving as torque transmitting elements that are arranged between track grooves 30 and 40 of the outer joint member 11 and the inner joint member 16, and a cage 44 having a spherical outer peripheral surface 45 and a spherical inner peripheral surface 46 that are fitted to a cylindrical inner peripheral surface 42 of the outer joint member 11 and a spherical outer peripheral surface 43 of the inner joint member 16, respectively, and being configured to retain the balls 41. A curvature center $O_1$ of the spherical outer peripheral surface 45 and a curvature center $O_2$ of the spherical inner peripheral surface 46 of the cage 44 are offset equidistantly from a joint center O toward opposite sides in the axial direction.

An inner ring of a support bearing 6 is fixed to an outer peripheral surface of the long stem section 13, and an outer ring of the support bearing 6 is fixed to a transmission case with a bracket (not shown). The outer joint member 11 is supported by the support bearing 6 in a freely rotatable manner, and when the support bearing 6 as described above is provided, vibration of the outer joint member 11 during driving or the like is prevented as much as possible.

The fixed type constant velocity universal joint 20 illustrated in FIG. 1 is a so-called Rzeppa type constant velocity universal joint, and comprises an outer joint member 21 comprising a bottomed cylindrical cup section 21a and a shaft section 21b that extends from a bottom portion of the cup section 21a in the axial direction, an inner joint member 22 housed along an inner periphery of the cup section 21a of the outer joint member 21, balls 23 serving as torque transmitting elements that are arranged between the cup section 21a of the outer joint member 21 and the inner joint member 22, and a cage 24, which is arranged between an inner peripheral surface of the cup section 21a of the outer joint member 21 and an outer peripheral surface of the inner joint member 22, and is configured to retain the balls 23. As the fixed type constant velocity universal joint 20, an undercut-free type constant velocity universal joint may sometimes be used.

The intermediate shaft 2 comprises splines 3 for torque transmission (including serrations; the same applies hereinafter) at outer diameters on both end portions thereof. The spline 3 on the inboard side is spline-fitted to a hole portion of the inner joint member 16 of the plunging type constant velocity universal joint 10. Thus, the intermediate shaft 2 and the inner joint member 16 of the plunging type constant velocity universal joint 10 are coupled to each other to allow torque transmission therebetween. Further, the spline 3 on the outboard side is spline-fitted to a hole portion of the inner joint member 22 of the fixed type constant velocity universal joint 20. Thus, the intermediate shaft 2 and the inner joint member 22 of the fixed type constant velocity universal joint 20 are coupled to each other to allow torque transmission therebetween. Although the solid intermediate shaft 2 is illustrated, a hollow intermediate shaft may be used instead.

Grease is sealed inside both the constant velocity universal joints 10 and 20 as a lubricant. To prevent leakage of the grease to an outside of the joint or entry of a foreign matter from the outside of the joint, bellows boots 4 and 5 are respectively mounted to a portion between the outer joint member 11 of the plunging type constant velocity universal joint 10 and the intermediate shaft 2 and a portion between the outer joint member 21 of the fixed type constant velocity universal joint 20 and the intermediate shaft 2.

The outer joint member manufactured based on the manufacturing method according to the first embodiment is described with reference to FIG. 2. FIG. 2 are enlarged views for illustrating the outer joint member 11. FIG. 2a is a partial vertical sectional view. FIG. 2b is an enlarged view of the portion A of FIG. 2a. FIG. 2c is a view for illustrating a shape before welding. The outer joint member 11 comprises the bottomed cylindrical cup section 12 that is opened at one end and has the cylindrical inner peripheral surface 42 and the plurality of track grooves 30, on which the balls 41 (see FIG. 1) are caused to roll, formed equiangularly on the inner peripheral surface, and the long stem section 13 that extends from the bottom portion of the cup section 12 in the axial direction and comprises a spline Sp serving as a torque transmitting coupling portion formed at an outer periphery on an end portion thereof on an opposite side to the cup section 12. The outer joint member 11 is formed by welding a cup member 12a and a shaft member 13a to each other.

The cup member 12a illustrated in FIG. 2a to FIG. 2c is an integrally-formed product being made of medium carbon steel, such as S53C, containing carbon of from 0.40 wt % to 0.60 wt %, and having a cylindrical portion 12a1 and a bottom portion 12a2. The cylindrical portion 12a1 has the track grooves 30 and the cylindrical inner peripheral surface 42 formed at an inner periphery thereof. A projecting portion 12a3 is formed at the bottom portion 12a2 of the cup member 12a. A boot mounting groove 32 is formed at an outer periphery of the cup member 12a on the opening side thereof, whereas a snap ring groove 33 is formed at an inner periphery of the cup member 12a on the opening side thereof. A bearing mounting surface 14 and a snap ring groove 15 are formed at an outer periphery of the shaft member 13a on the cup member 12a side, whereas the spline Sp is formed at an end portion of the shaft member 13a on an opposite side.

The shaft member 13a is made of medium carbon steel, such as S40C, containing carbon of from 0.30 wt % to 0.55 wt %. A joining end surface 50 formed at the projecting portion 12a3 of the bottom portion 12a2 of the cup member 12a and a joining end surface 51 formed at an end portion of the shaft member 13a on the cup member 12a side are brought into abutment against each other, and are welded to each other by electron beam welding performed from an outer side of the cup member 12a in a radial direction. As illustrated in FIG. 2a and FIG. 2b, a welded portion 49 (hereinafter also referred to as "weld bead 49") is formed of a bead, which is formed by a beam radiated from a radially outer side of the cup member 12a. Although detailed description is made later, outer diameters B1 and B2 of the joining end surface 50 and the joining end surface 51 (see FIG. 4b and FIG. 5c) are set to equal dimensions for each joint size. However, the outer diameter B1 of the joining end surface 50 of the cup member 12a and the outer diameter B2 of the joining end surface 51 of the shaft member 13a need not be set to equal dimensions. In consideration of, for example, a state of the weld bead, a dimensional difference may be given as appropriate in such a manner that the outer diameter B2 of the joining end surface 51 is set slightly smaller than the outer diameter B1 of the joining end surface 50, or that the outer diameter B2 of the joining end surface 51 is set slightly larger than the outer diameter B1 of the joining end surface 50, conversely. The description "the outer diameters B1 and B2 of the joining end surface 50 and the joining end surface 51 are set to equal dimensions for each joint size" herein refers to a concept encompassing a case in which the dimensional difference is given as appropriate between the outer diameter B1 of the joining end surface 50 and the outer diameter B2 of the joining end surface 51.

As illustrated in FIG. 2a to FIG. 2c, the welded portion 49 is formed on the joining end surface 51 located on the cup member 12a side with respect to the bearing mounting surface 14 of the shaft member 13a, and hence the bearing mounting surface 14 and the like can be processed in advance so that post-processing after welding can be omitted. Further, the electron beam welding does not cause formation of burrs at the welded portion. Thus, post-processing for the welded portion can also be omitted, thereby being capable of reducing manufacturing cost. Still further, total inspection on the welded portion through ultrasonic flaw detection can be performed. As a feature, the manufacturing method according to the first embodiment comprises an ultrasonic flaw detection-inspection step which enables defect detection for a welded portion of an outer joint member of a constant velocity universal joint being a mass-produced product with high detection accuracy and in a wide detection range and also at the level of enabling industrial production. Details thereof are described later.

As illustrated in FIG. 2c, the joining end surface 50 of the cup member 12a is formed by annular turning, and a center portion in a radial direction maintains a forged surface. With this, a turning time is shortened. An annular groove portion 51a is formed on a radially inner side of the joining end surface 51 of the shaft member 13a, and an annular blocking portion 51b is formed more on a radially inner side. The annular groove portion 51a is formed in a weld joint interface directly below a weld bead 49 (see FIG. 2b). When the both joining end surfaces 50 and 51 are brought into abutment against each other, a hollow cavity portion H is formed. The annular groove portion 51a and the hollow cavity portion H are separated and blocked by the annular blocking portion 51b. The welded portion 49 having the annular groove portion 51a and the annular blocking portion 51b has a complicated workpiece shape subjected to ultrasonic flaw detection-inspection described later.

When the cup member 12a and the shaft member 13a described above are brought into abutment against each other, and electron beam welding is performed in a vacuum (low pressure) atmosphere at the level of enabling industrial production of a constant velocity universal joint being a mass-produced product, no recess is formed on the radially inner side of the weld bead 49 as illustrated in FIG. 2b. Further, the radially inner end portion of the weld bead 49 is sufficiently formed to reach the annular groove portion 51a. It is considered that the internal pressure of residual air in the hollow cavity portion H is blocked by the annular blocking portion 51b, or a volume of the residual air in the annular groove portion 51*a* is small, and hence the amount of expansion in volume due to heating is small, thereby suppressing the influence of the internal pressure. With this configuration, the strength, quality, and reliability of the welded portion can be improved. The annular groove portion 51*a* has a width of from about 1 mm to about 3 mm and a depth of from about 0.5 mm to 2 mm.

Figure 3:
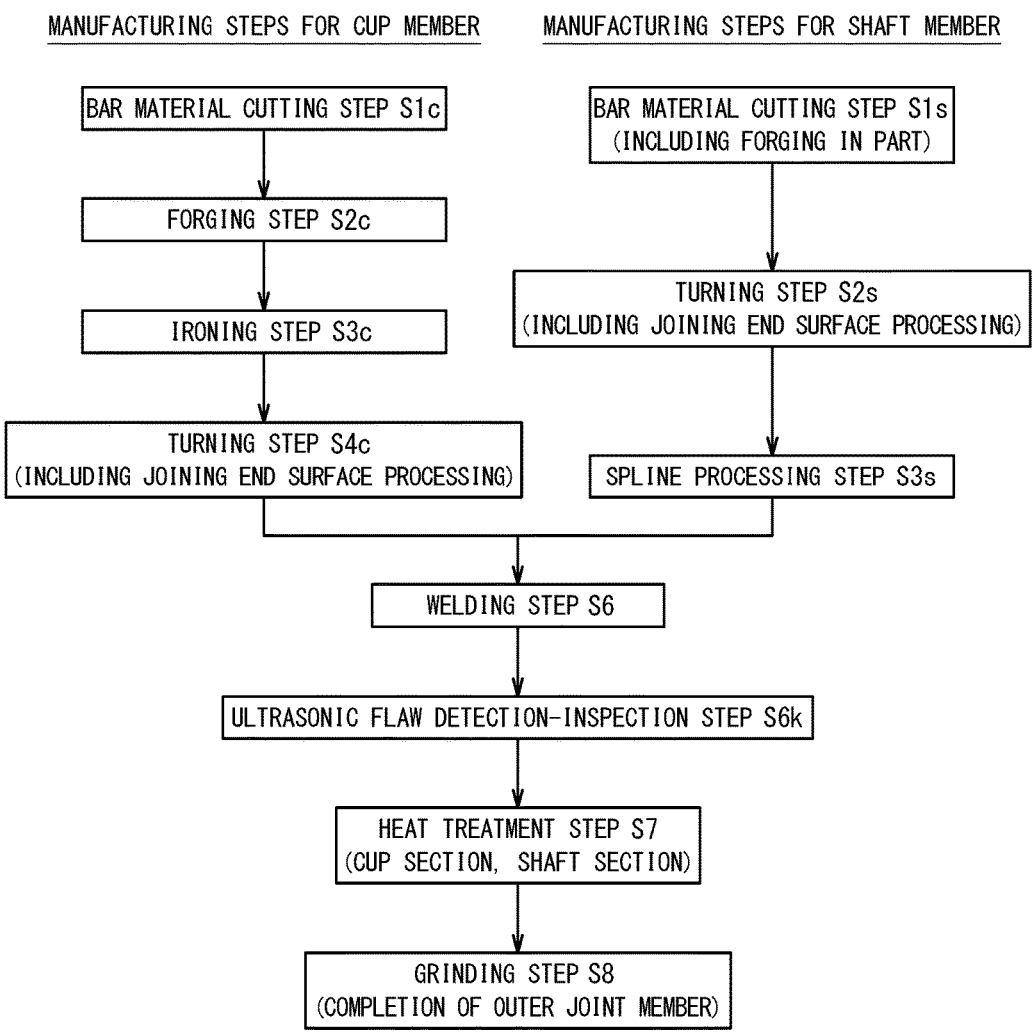
FIG. 3 is an illustration of an overview of manufacturing steps for the outer joint member of FIG. 1.

Next, the manufacturing method according to the first embodiment of the present invention is described with reference to FIG. 3 to FIG. 22. Before description of details of the features of the manufacturing method according to the first embodiment, that is, an ultrasonic flaw detection-inspection step for the welded portion, an overview of manufacturing steps (processing steps) is described. FIG. 3 is an illustration of the overview of the manufacturing steps for the outer joint member. In the first embodiment, as illustrated in FIG. 3, the cup member 12*a* is manufactured through manufacturing steps comprising a bar material cutting step S1*c*, a forging step S2*c*, an ironing step S3*c*, and a turning step S4*c*. Meanwhile, the shaft member 13*a* is manufactured through manufacturing steps comprising a bar material cutting step S1*s*, a turning step S2*s*, and a spline processing step S3*s*. Intermediate components of the cup member 12*a* and the shaft member 13*a* thus manufactured are each assigned with a product number for management.

After that, the cup member 12*a* and the shaft member 13*a* are subjected to a welding step S6, an ultrasonic flaw detection-inspection step S6*k*, a heat treatment step S7, and a grinding step S8 so that the outer joint member 11 is completed.

An overview of each step is described. Each step is described as a typical example, and appropriate modification and addition may be made to each step as needed. First, the manufacturing steps for the cup member 12*a* are described.

[Bar Material Cutting Step S1*c*]

A bar material is cut into a predetermined length in accordance with a forging weight, thereby producing a billet.

[Forging Step S2*c*]

The billet is subjected to forging so as to integrally form the cylindrical portion, the bottom portion, and the projecting portion as a preform of the cup member 12*a*.

[Ironing Step S3*c*]

Ironing is performed on the track grooves 30 and the cylindrical inner peripheral surface 42 of the preform, thereby finishing the inner periphery of the cylindrical portion of the cup member 12*a*.

[Turning Step S4*c*]

In the preform after ironing, the outer peripheral surface, the boot mounting groove 32, the snap ring groove 33, the joining end surface 50, and the like are formed by turning. In the first embodiment, after the turning step S4*c*, the cup member 12*a* in the form of an intermediate component is assigned with a product number for management.

Next, the manufacturing steps for the shaft member 13*a* are described.

[Bar Material Cutting Step S1*s*]

A bar material is cut into a predetermined length in accordance with the entire length of the shaft section, thereby producing a billet. After that, the billet is forged into a rough shape by upset forging depending on the shape of the shaft member 13*a* in some cases.

[Turning Step S2*s*]

The outer peripheral surface of the billet or the preform (bearing mounting surface 14, snap ring groove 15, minor diameter of the spline, end surface, and the like), the joining end surface 51 of the billet at the end portion on the cup member 12*a* side, and the annular groove portion 51*a* are formed by turning.

[Spline Processing Step S3*s*]

The spline is formed by rolling in the shaft member after turning. Note that, the processing for the spline is not limited to the rolling, and press working or the like may be adopted instead as appropriate. In the first embodiment, after the spline processing, the shaft member 13*a* in the form of an intermediate component is assigned with a product number for management.

Next, the manufacturing steps in the process of completing the outer joint member 11 from the cup member 12*a* and the shaft member 13*a* are described.

[Welding Step S6]

The joining end surface 50 of the cup member 12*a* and the joining end surface 51 of the shaft member 13*a* are brought into abutment against each other and welded.

[Ultrasonic Flaw Detection-Inspection Step S6*k*]

The welded portion 49 between the cup member 12*a* and the shaft member 13*a* is inspected by the ultrasonic flaw-detection method.

[Heat Treatment Step S7]

Induction quenching and tempering are performed as heat treatment on at least the track grooves 30 and the cylindrical inner peripheral surface 42 of the cup section 12 after welding and a necessary range of the outer periphery of the shaft section 13 after welding. Heat treatment is not performed on the welded portion. A hardened layer having a hardness of approximately from 58 HRC to 62 HRC is formed on each of the track grooves 30 and the cylindrical inner peripheral surface 42 of the cup section 12. Further, a hardened layer having a hardness of approximately from 50 HRC to 62 HRC is formed in a predetermined range of the outer periphery of the shaft section 13.

[Grinding Step S8]

After the heat treatment, the bearing mounting surface 14 of the shaft section 13 and the like are finished by grinding. Thus, the outer joint member 11 is completed.

In the manufacturing steps of the first embodiment, the heat treatment step is provided after the welding step, and hence the manufacturing steps are suited to a cup member and a shaft member having such shapes and specifications that the hardness of the heat-treated portion may be affected by temperature rise at the periphery due to heat generated during the welding.

Figure 4A:
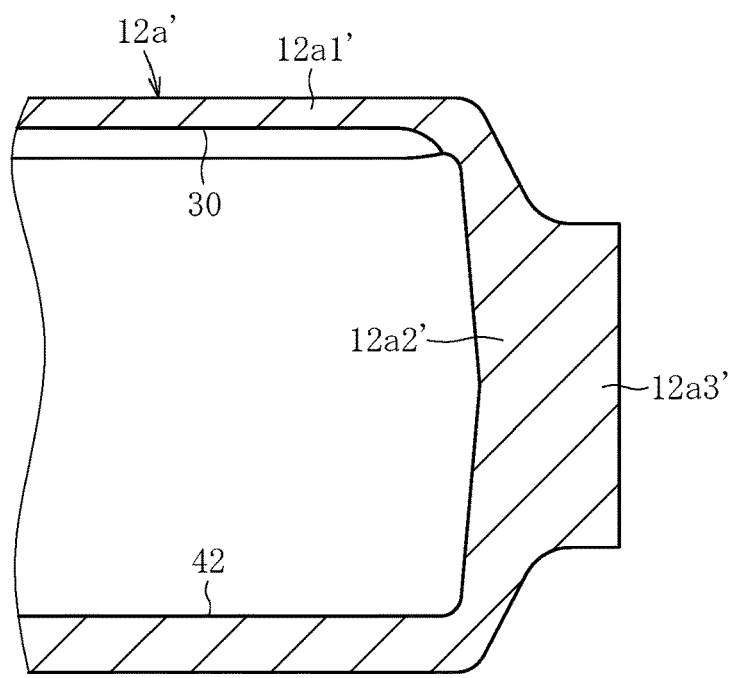
FIG. 4a is a vertical sectional view for illustrating a cup member before welding and after ironing.
Figure 4B:
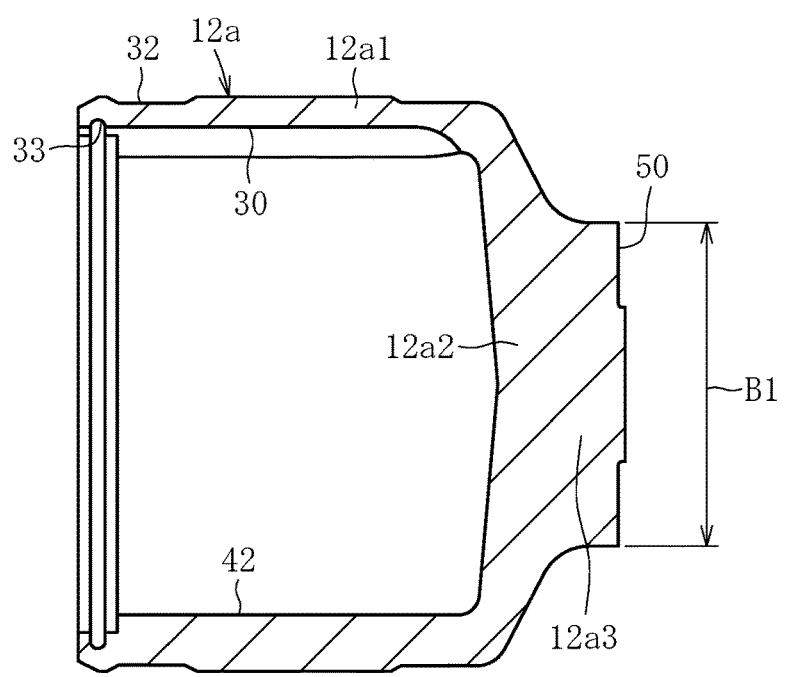
FIG. 4b is a vertical sectional view for illustrating the cup member before welding and after turning.

Next, main constituent features of the manufacturing method of the first embodiment are described in detail. FIG. 4*a* is a vertical sectional view for illustrating a state after ironing of the cup member 12*a*. FIG. 4*b* is a vertical sectional view for illustrating a state after turning. In a preform 12*a*' for the cup member 12*a*, a cylindrical portion 12*a*1', a bottom portion 12*a*2', and a projecting portion 12*a*3' are integrally formed in the forging step S2*c*. After that, the track grooves 30 and the cylindrical inner peripheral surface 42 are formed by ironing in the ironing step S3*c* so that the inner periphery of the cylindrical portion 12*a*1' is finished as illustrated in FIG. 4*a*.

After that, in the turning step S4*c*, the outer peripheral surface, the boot mounting groove 32, the snap ring groove 33, and the like of the cup member 12*a* as well as the joining end surface 50 of the projecting portion 12*a*3 of the bottom portion 12*a*2, and the outer diameter B1 portion thereof are formed by turning as illustrated in FIG. 4*b*.

Figure 5A:
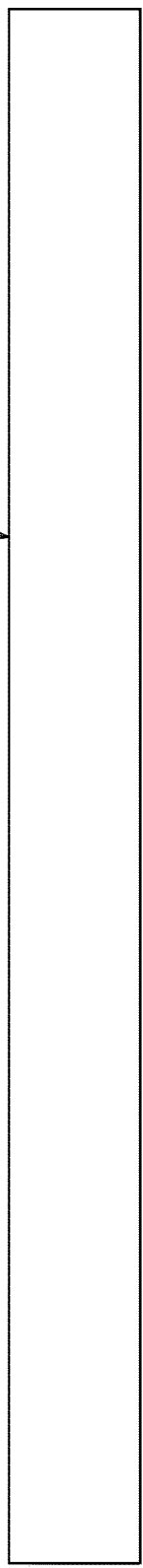
FIG. 5a is a front view for illustrating a shaft member before welding, which is a billet obtained by cutting a bar material.

FIG. 5 are illustrations of states of the shaft member 13*a* in the respective processing steps. FIG. 5*a* is a front view for illustrating a billet 13*a*" obtained by cutting a bar material.

Figure 5B:
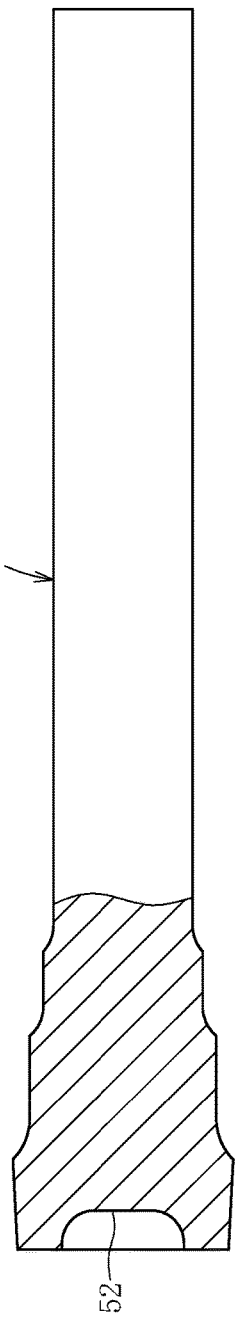
FIG. 5b is a partial vertical sectional view for illustrating the shaft member before welding and after forging.
Figure 5C:
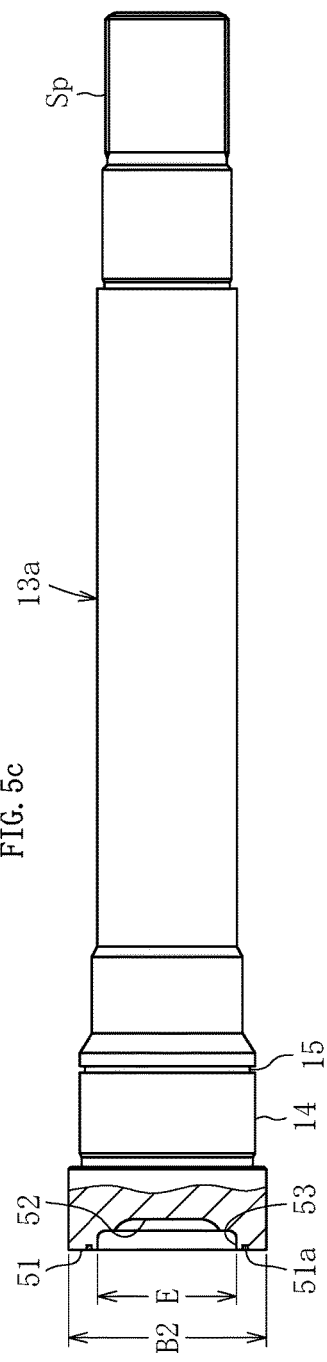
FIG. 5c is a partial vertical sectional view for illustrating the shaft member before welding and after turning and spline processing.

FIG. 5b is a partial vertical sectional view for illustrating a preform 13a' obtained by forging the billet 13a" into a rough shape by upset forging. FIG. 5c is a partial vertical sectional view for illustrating the shaft member 13a after turning and spline processing.

The billet 13a" illustrated in FIG. 5a is produced in the bar material cutting step S1s. The preform 13a' is produced by increasing the shaft diameter of the billet 13a" in a predetermined range and forming a recessed portion 52 at a joining-side end portion (end portion on the cup member 12a side) by upset forging as needed as illustrated in FIG. 5b.

After that, in the turning step S2s, the outer diameter portion of the shaft member 13a, the bearing mounting surface 14, the snap ring groove 15, an inner diameter surface 53 (inner diameter E) of the recessed portion 52, the joining end surface 51, the outer diameter B2 portion thereof, and the annular groove portion 51a are formed by turning as illustrated in FIG. 5c. In the spline processing step S3s, the spline Sp is processed at the end portion on the opposite side to the recessed portion 52 by rolling or press forming.

The outer diameter B1 of the joining end surface 50 of the cup member 12a illustrated in FIG. 4b is set to an equal dimension for one joint size. Further, in the shaft member 13a illustrated in FIG. 5c, which is used as a long stem shaft, the outer diameter B2 of the joining end surface 51 is set to an equal dimension for one joint size irrespective of the shaft diameter and the outer peripheral shape. Still further, the joining end surface 51 of the shaft member 13a is located at the position on the cup member 12a side with respect to the bearing mounting surface 14. Through the setting of dimensions as described above, the outer joint member 11 compatible with various vehicle types can be manufactured in such a manner that, while the cup member 12a is prepared for common use, only the shaft member 13a is manufactured to have a variety of shaft diameters, lengths, and outer peripheral shapes depending on vehicle types, and both the members 12a and 13a are welded to each other. Details of the preparation of the cup member 12a for common use are described later.

Figure 6:
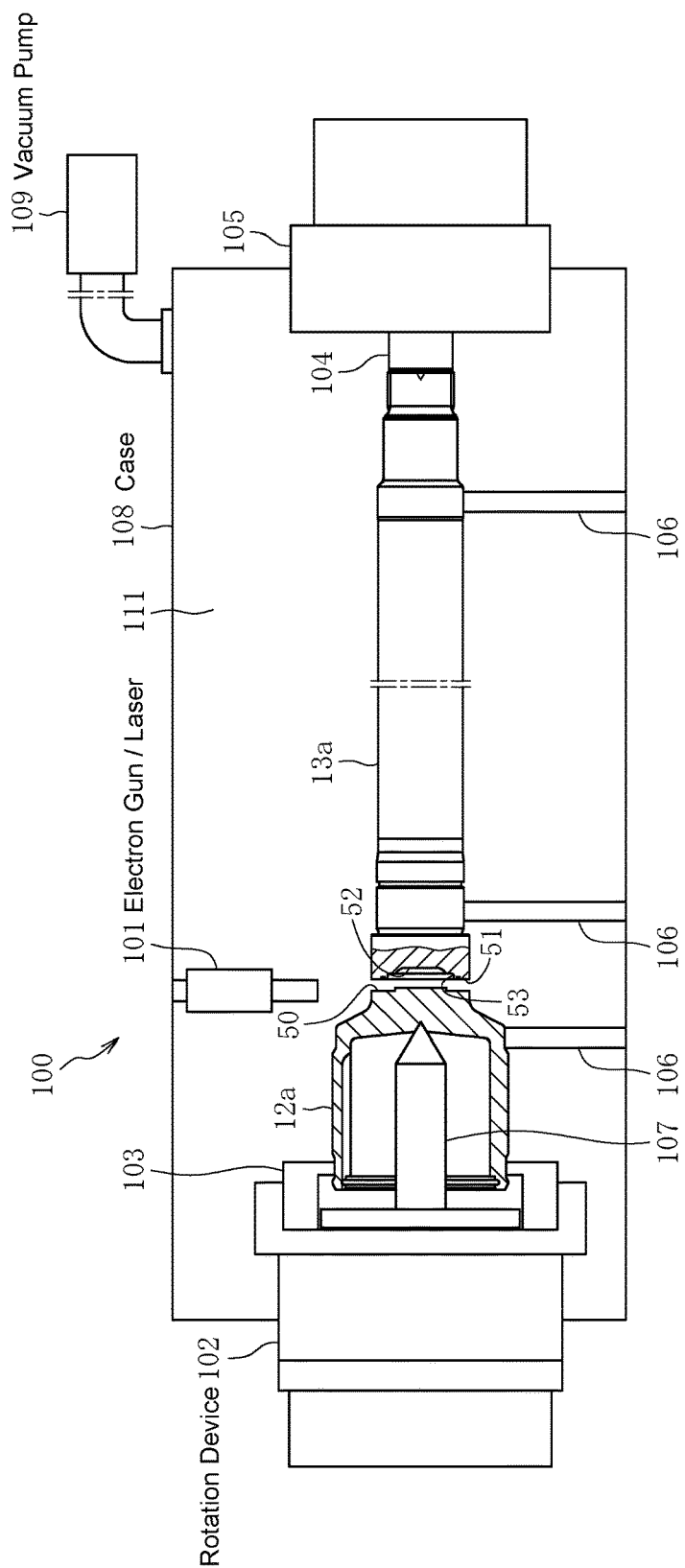
FIG. 6 is a view for illustrating an overview of a welding step.
Figure 7:
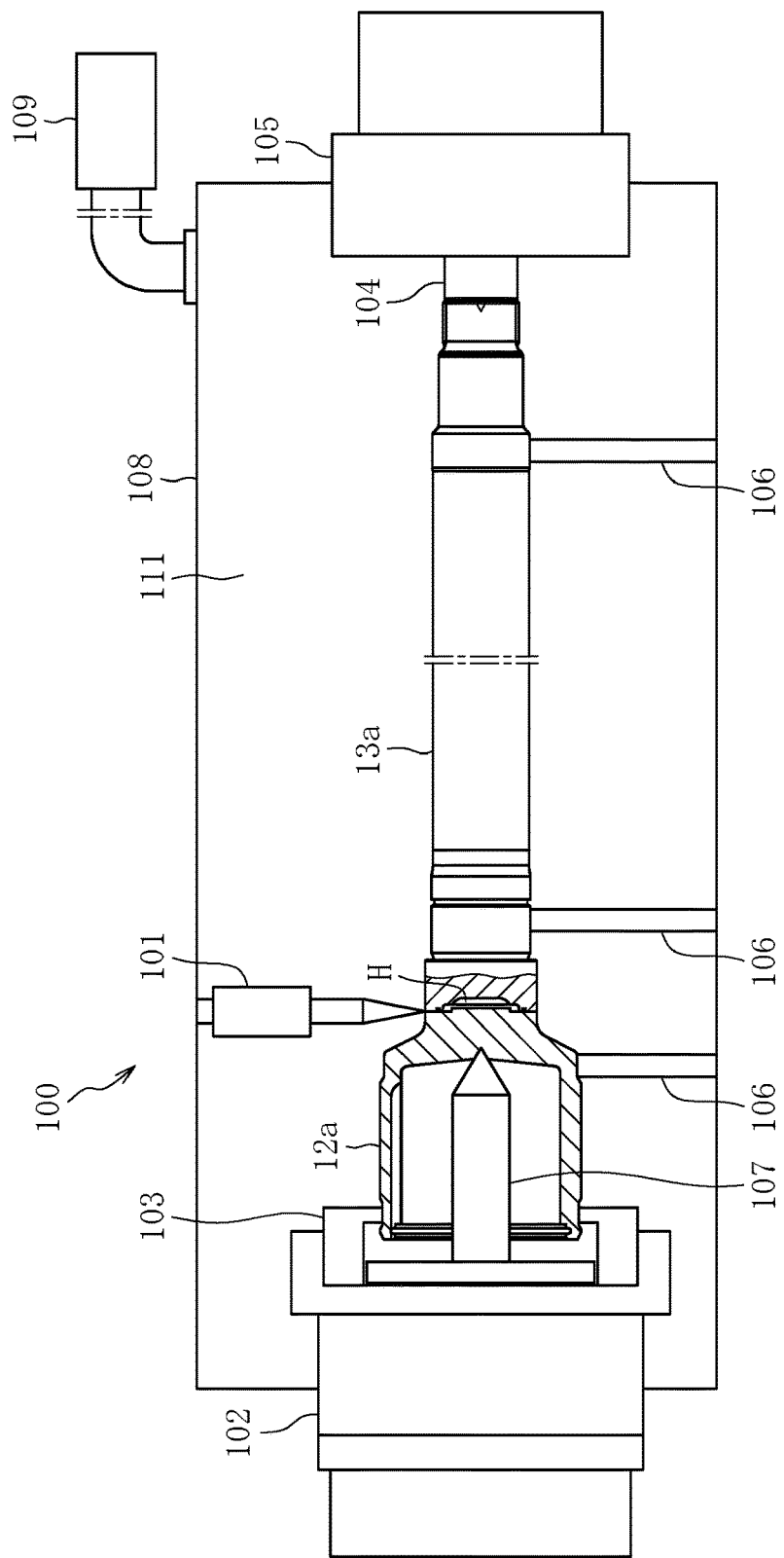
FIG. 7 is a view for illustrating an overview of the welding step.

Next, a method of welding the cup member 12a and the shaft member 13a is described with reference to FIG. 6 and FIG. 7. FIG. 6 and FIG. 7 are views for illustrating an overview of a welding apparatus. FIG. 6 is an illustration of a state before welding. FIG. 7 is an illustration of a state during welding. As illustrated in FIG. 6, a welding apparatus 100 mainly comprises an electron gun 101, a rotation device 102, a chuck 103, a center hole guide 104, a tailstock 105, workpiece supports 106, a center hole guide 107, a case 108, and a vacuum pump 109.

The cup member 12a and the shaft member 13a being workpieces are placed on the workpiece supports 106 arranged inside the welding apparatus 100. The chuck 103 and the center hole guide 107 arranged at one end of the welding apparatus 100 are coupled to the rotation device 102. The chuck 103 grips the cup member 12a under a state in which the centering of the cup member 12a is performed by the center hole guide 107, thereby applying rotational movement. The center hole guide 104 is integrally mounted to the tailstock 105 arranged at another end of the welding apparatus 100. Both the center hole guide 104 and the tailstock 105 are configured to reciprocate in the axial direction (right-and-left direction in FIG. 6 and FIG. 7).

A center hole of the shaft member 13a is set on the center hole guide 104 so that the centering of the shaft member 13a is performed. The vacuum pump 109 is connected to the case 108 of the welding apparatus 100. A "sealed space" herein refers to a space 111 defined by the case 108. In the first embodiment, the cup member 12a and the shaft member 13a are entirely received in the sealed space 111. The electron gun 101 is arranged at a position corresponding to the joining end surfaces 50 and 51 of the cup member 12a and the shaft member 13a. The electron gun 101 is configured to approach the workpieces up to a predetermined position.

Next, the operation of the welding apparatus 100 constructed as described above and the welding method are described. The cup member 12a and the shaft member 13a being workpieces are stocked at a place different from the place of the welding apparatus 100. The respective workpieces are taken out by, for example, a robot, are conveyed into the case 108 of the welding apparatus 100 opened to the air as illustrated in FIG. 6, and are set at predetermined positions on the workpiece supports 106. At this time, the center hole guide 104 and the tailstock 105 retreat to the right side of FIG. 6, and hence a gap is formed between the joining end surfaces 50 and 51 of the cup member 12a and the shaft member 13a. After that, a door (not shown) of the case 108 is closed, and the vacuum pump 109 is activated to reduce the pressure in the sealed space 111 defined in the case 108. Thus, the pressures in the recessed portion 52 and the inner diameter portion 53 of the shaft member 13a are reduced as well.

When the pressure in the sealed space 111 is reduced to a predetermined pressure, the center hole guide 104 and the tailstock 105 are caused to advance to the left side as illustrated in FIG. 7 to eliminate the gap between the joining end surfaces 50 and 51 of the cup member 12a and the shaft member 13a. With this action, the cavity portion H which is reduced in pressure is formed between the joining end surface 50 of the cup member 12a and the inner diameter surface 53 and the recessed portion 52 of the shaft member 13a, and the annular groove portion 51a which is reduced in pressure is formed while being blocked by the annular blocking portion 51b (see FIG. 2c) from the hollow cavity portion H. The centering of the cup member 12a is performed by the center hole guide 107, and is fixed by the chuck 103, whereas the shaft member 13a is supported by the center hole guide 104. After that, the workpiece supports 106 are moved away from the workpieces. At this time, the distance between the workpiece supports 106 and the workpieces may be infinitesimal, and hence illustration of this distance is omitted from FIG. 7. As a matter of course, the welding apparatus 100 may have such a structure that the workpiece supports 106 retreat downward greatly.

Although illustration is omitted, the electron gun 101 is then caused to approach the workpieces up to a predetermined position, and the workpieces are rotated to start pre-heating. As a pre-heating condition, unlike the welding condition, the temperature is set lower than the welding temperature by, for example, radiating an electron beam under a state in which the electron gun 101 is caused to approach the workpieces so as to increase the spot diameter. Through the pre-heating, the cooling rate after welding is reduced, thereby being capable of preventing a quenching crack. When a predetermined pre-heating time has elapsed, the electron gun 101 retreats to a predetermined position, and radiates the electron beam from the outer side of the workpieces in the radial direction to start welding. When the welding is terminated, the electron gun 101 retreats, and rotation of the workpiece is stopped.

Although illustration is omitted, the sealed space 111 is then opened to the air. Then, under a state in which the workpiece supports 106 are raised to support the workpieces, the center hole guide 104 and the tailstock 105 retreat to the right side, and the chuck 103 is opened. After that, for example, the robot grips the workpieces, takes the workpieces out of the welding apparatus 100, and places the workpieces into alignment on a cooling stocker. In the first embodiment, the cup member 12a and the shaft member 13a are entirely received in the sealed space 111, and hence the configuration of the sealed space 111 defined in the case 108 can be simplified.

Specifically, the cup member 12a having a carbon content of from 0.4% to 0.6% and the shaft member 13a having a carbon content of from 0.3% to 0.55% were used and welded to each other in the above-mentioned welding apparatus 100 under the condition that the pressure in the sealed space 111 defined in the case 108 was set to 6.7 Pa or less. In order to prevent the cup member 12a and the shaft member 13a from being cooled rapidly after the welding to suppress increase in hardness of the welded portion, the joining end surfaces 50 and 51 of the cup member 12a and the shaft member 13a were soaked by pre-heating to have a temperature of from 300° C. to 650° C., and then electron beam welding was performed. As a result, a welded portion having no recess on a radially inner side of a weld bead was obtained. Further, through the soaking by pre-heating, the hardness of the welded portion after completion of the welding was able to be kept within a range of from 200 Hv to 500 Hv, thereby being capable of attaining high welding strength and stable welding state and quality. Still further, the cup member 12a and the shaft member 13a were welded to each other under the condition that the pressure in the sealed space 111 of the welding apparatus 100 was set to an atmospheric pressure or less, thereby being capable of suppressing the change in pressure in the hollow cavity portion during the welding. As a result, the blowing of a molten material and the entry of the molten material toward the radially inner side were able to be prevented. Setting of the pressure in the sealed space 111 defined in the case 108 to 6.7 Pa or less is a vacuum (low pressure) condition at the level of enabling industrial production of the constant velocity universal joint being a mass-produced product for automobiles and the like.

In the outer joint member 11 of the first embodiment, as illustrated in FIG. 2b, the annular groove portion 51a is formed in a weld joint interface directly below the weld bead 49 on the radially inner side of the joining end surface 51 of the shaft member 13a, and the annular blocking portion 51b is formed more on a radially inner side. The annular groove portion 51a and the hollow cavity portion H are separated and blocked by the annular blocking portion 51b.

It has been found that, when the cup member 12a and the shaft member 13a having the configuration descried above are brought into abutment against each other, and electron beam welding is performed, as illustrated in FIG. 2b, no recess is formed on the radially inner side of the weld bead 49, and the radially inner end portion of the weld bead 49 is sufficiently formed to reach the annular groove portion 51a. It is considered that the internal pressure in the hollow cavity portion H is blocked by the annular blocking portion 51b, or a volume of the residual air in the annular groove portion 51a is small, and hence the amount of expansion in volume due to heating is small, thereby suppressing the influence of the internal pressure. With this configuration, the strength, quality, and reliability of the welded portion can be improved.

Figure 8:
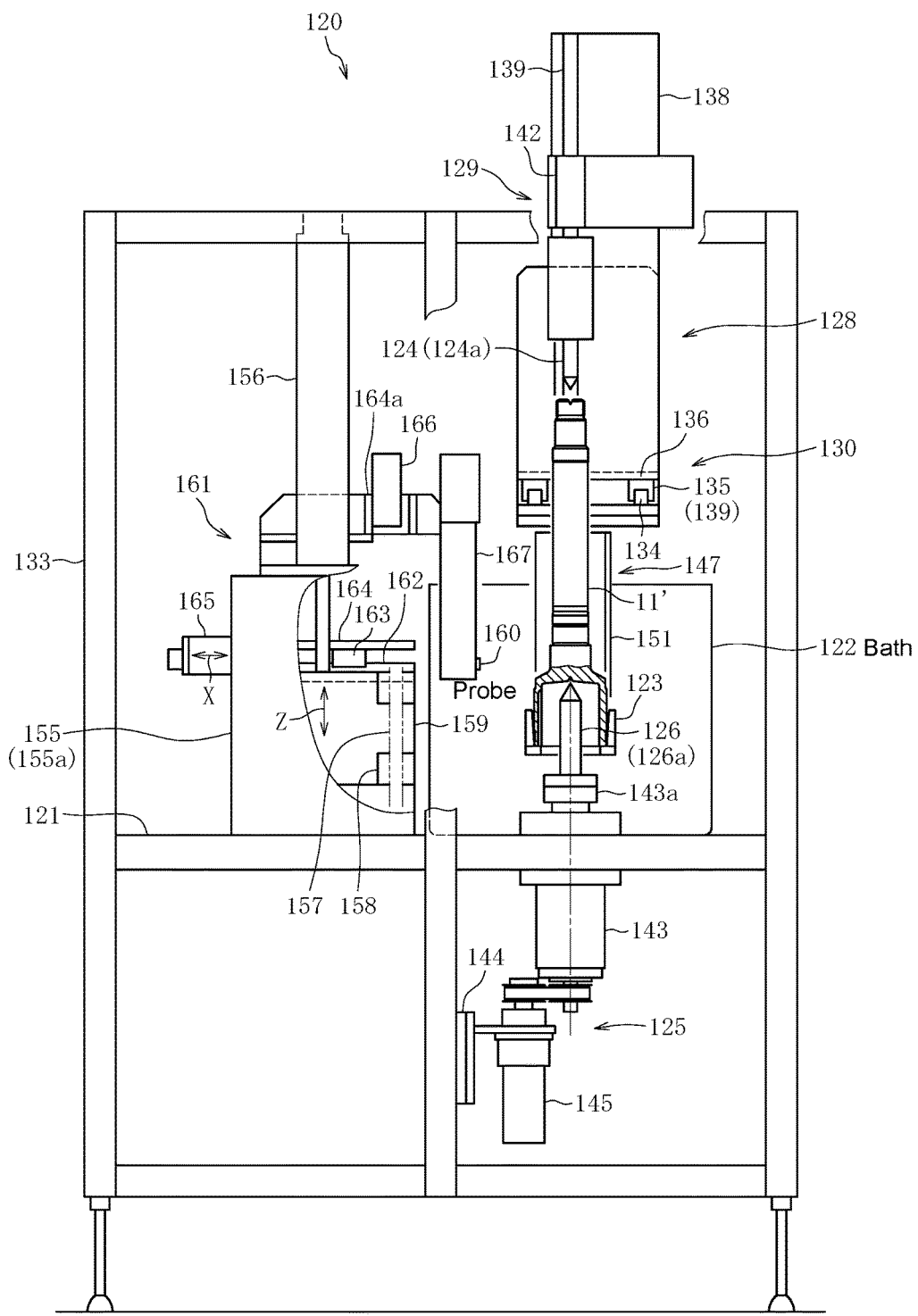
FIG. 8 is a front view for illustrating an overview of an ultrasonic flaw detection-inspection apparatus.
Figure 9:
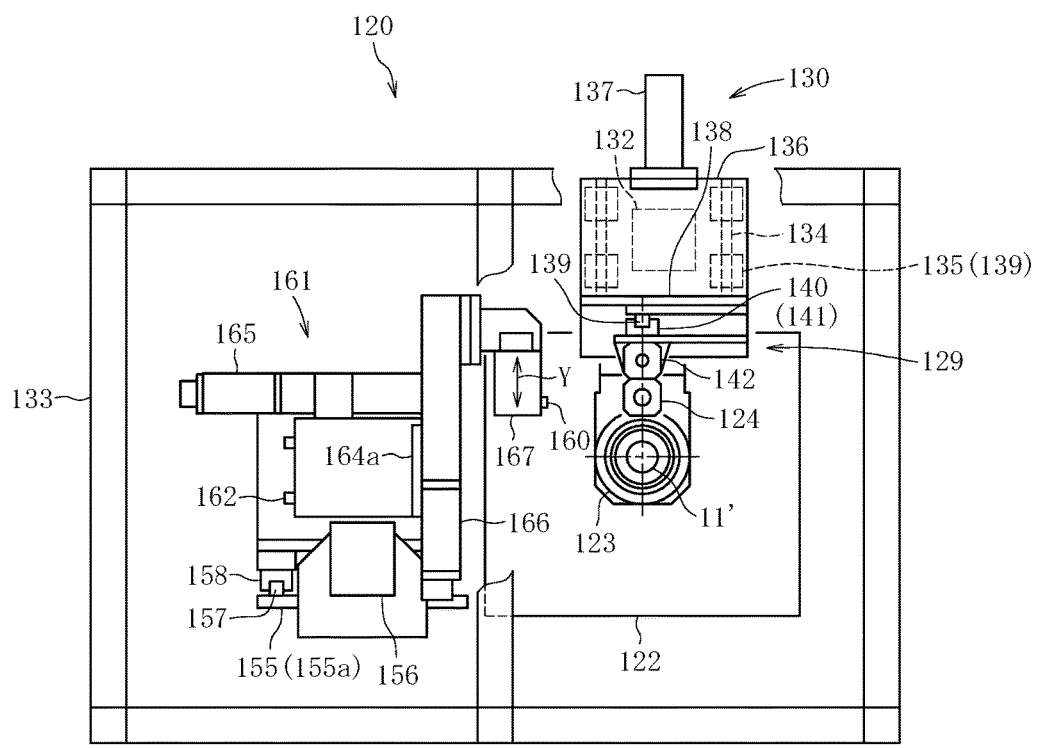
FIG. 9 is a plan view for illustrating an overview of the ultrasonic flaw detection-inspection apparatus.
Figure 10:
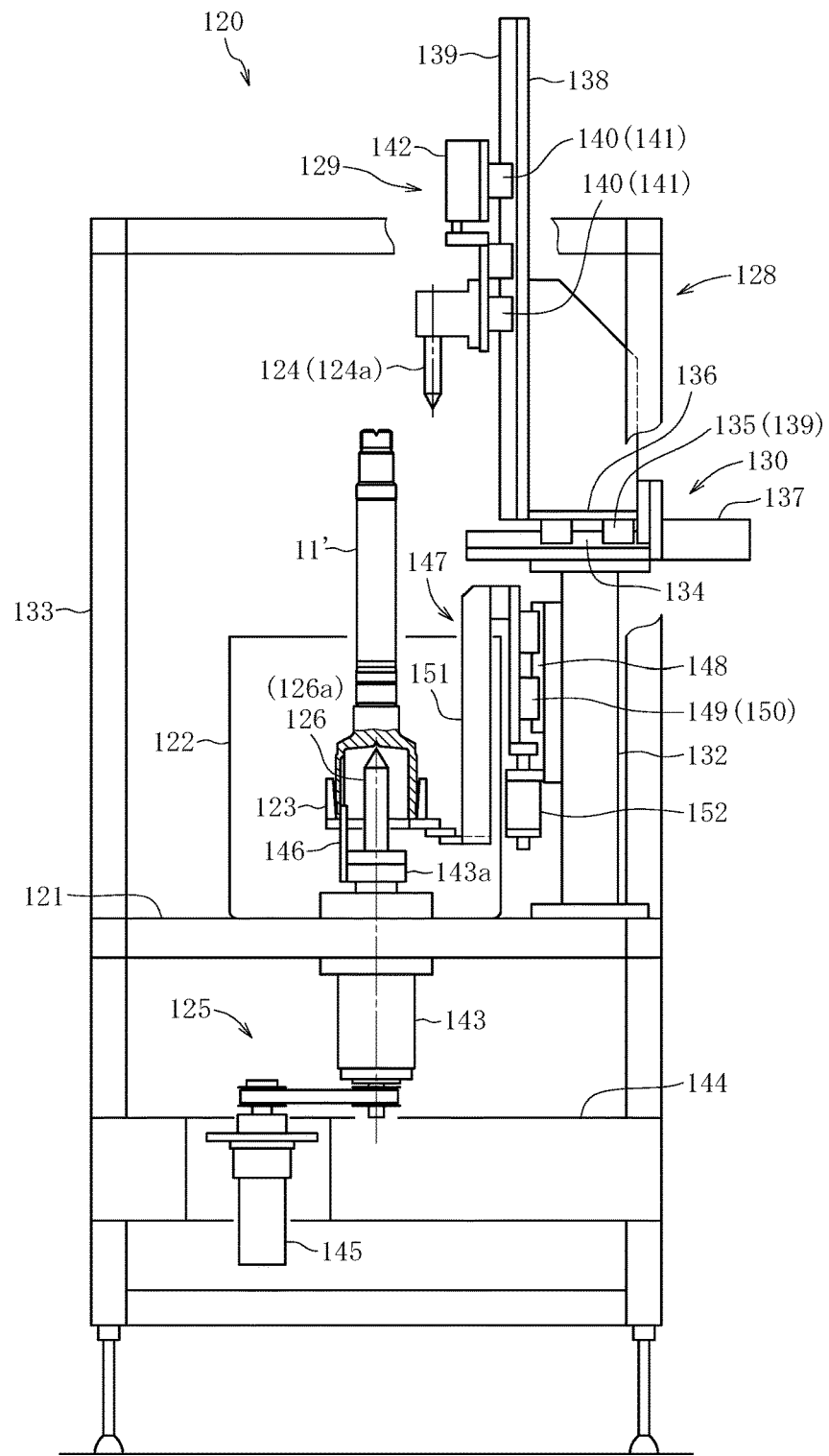
FIG. 10 is a right side view for illustrating an overview of the ultrasonic flaw detection-inspection apparatus.
Figure 11:
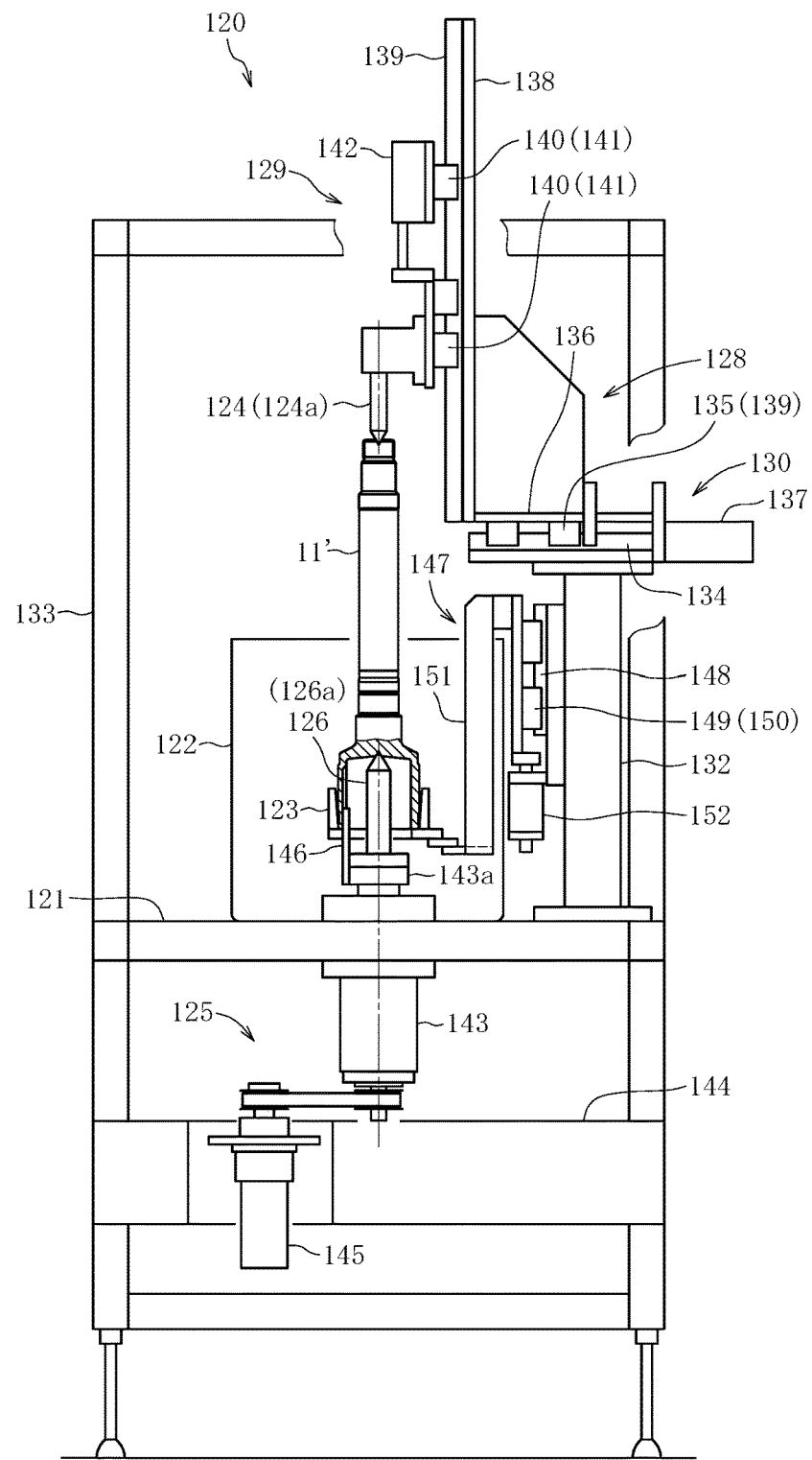
FIG. 11 is a right side view for illustrating an overview of the ultrasonic flaw detection-inspection apparatus.
Figure 12:
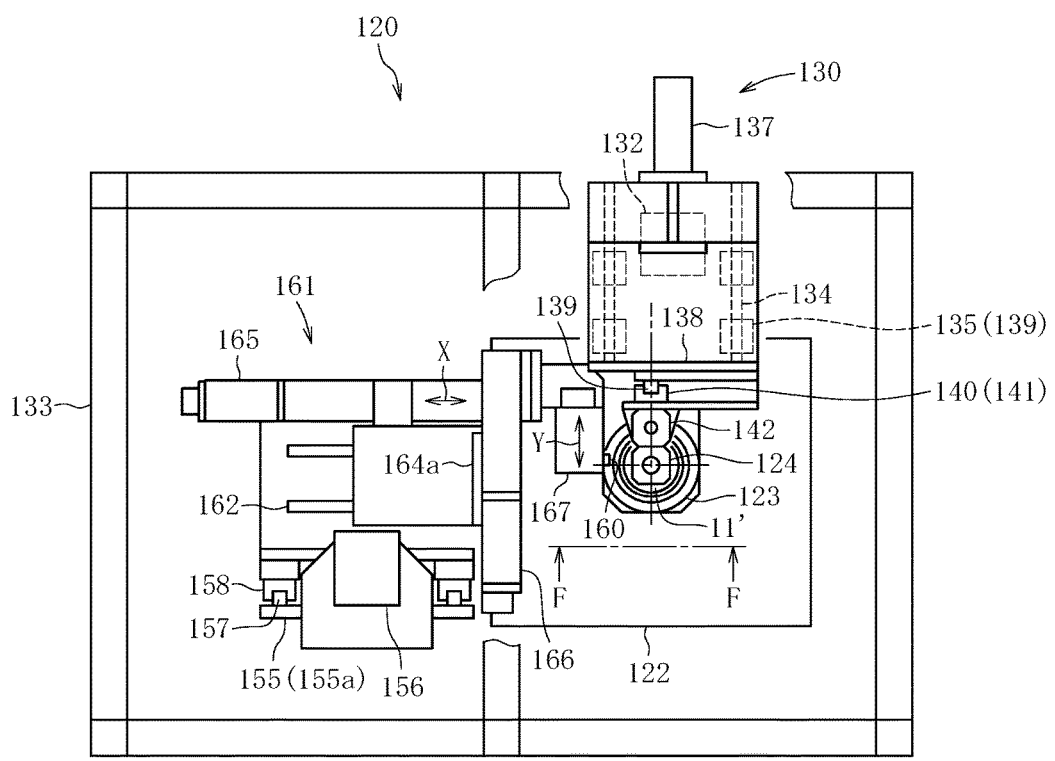
FIG. 12 is a plan view for illustrating an overview of the ultrasonic flaw detection-inspection apparatus.
Figure 13:
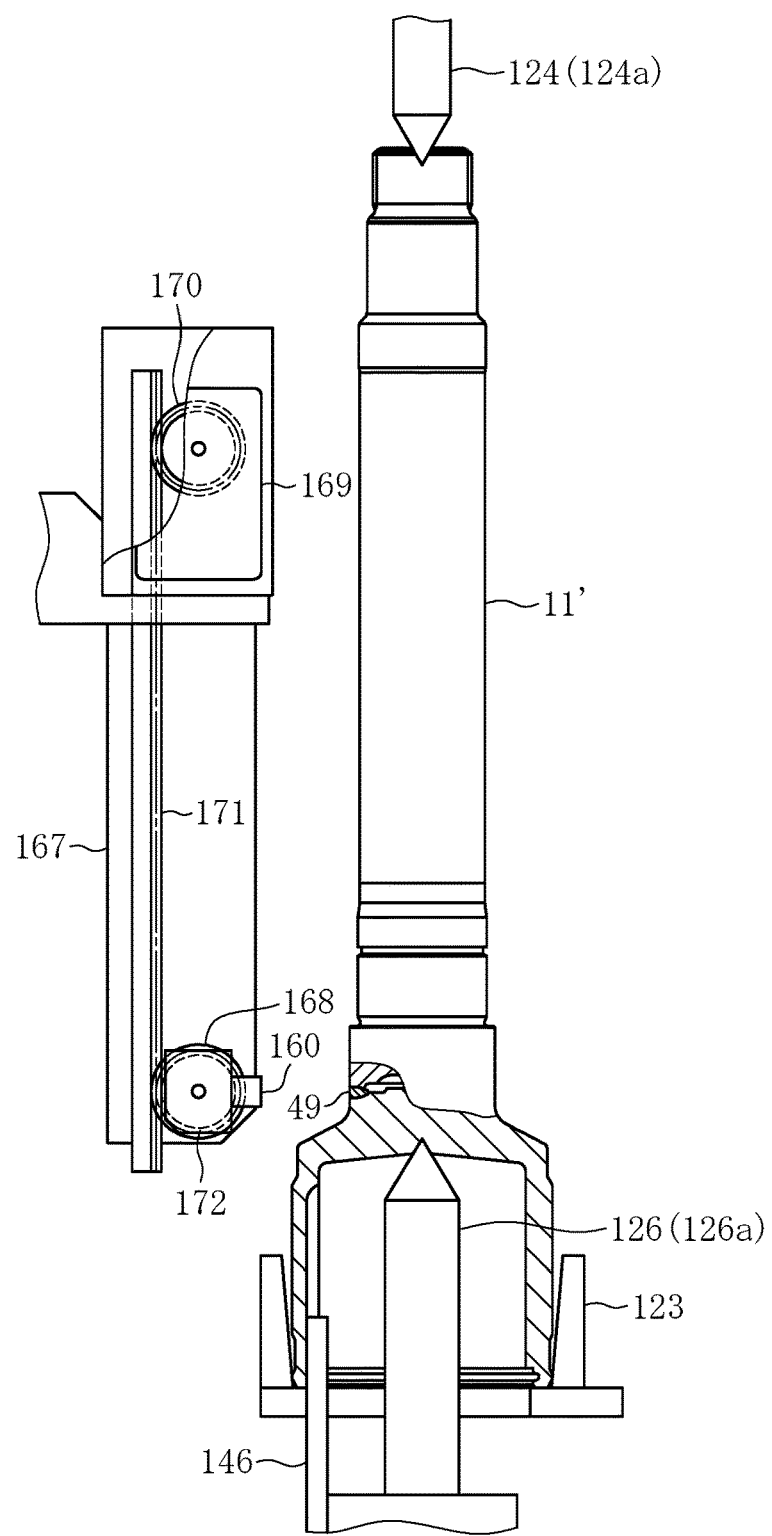
FIG. 13 is a partial enlarged view as seen from a direction indicated by the arrows of the line F-F of FIG. 12.
Figure 16A:
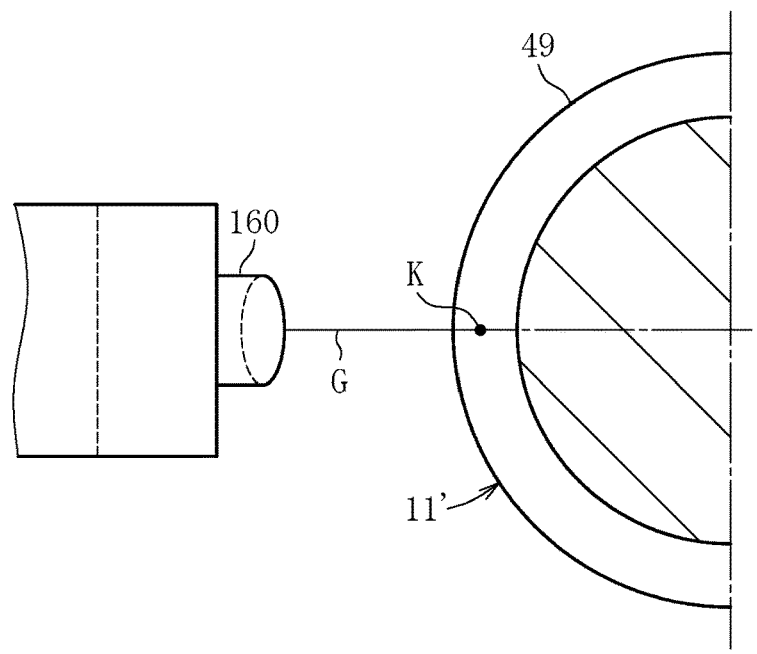
FIG. 16a is an illustration of a state of inspection by the axial angle beam flaw detection method, and is a partial cross-sectional view taken along the line I-I of FIG. 16b.
Figure 16B:
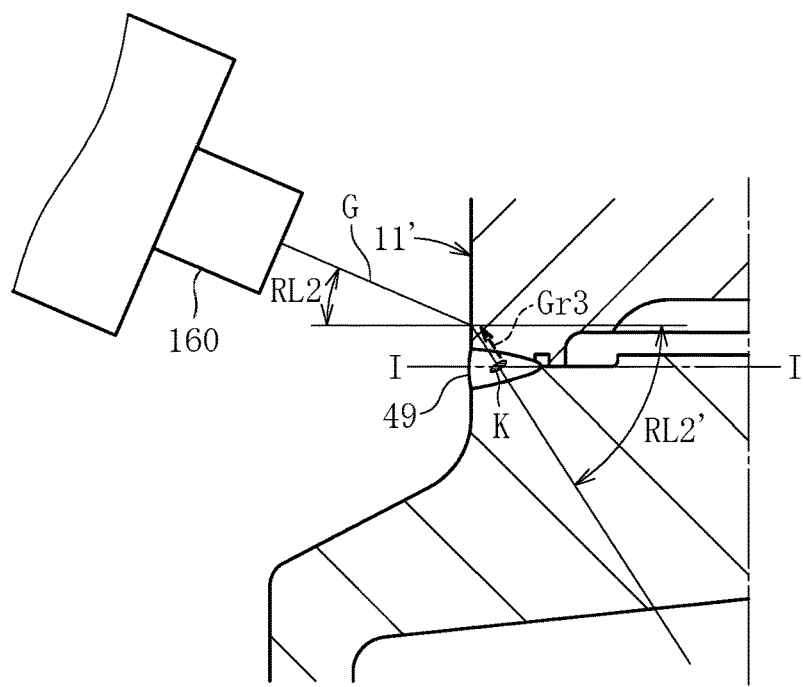
FIG. 16b is an illustration of a state of inspection by the axial angle beam flaw detection method, and is a partial vertical sectional view of the outer joint member.
Figure 17:
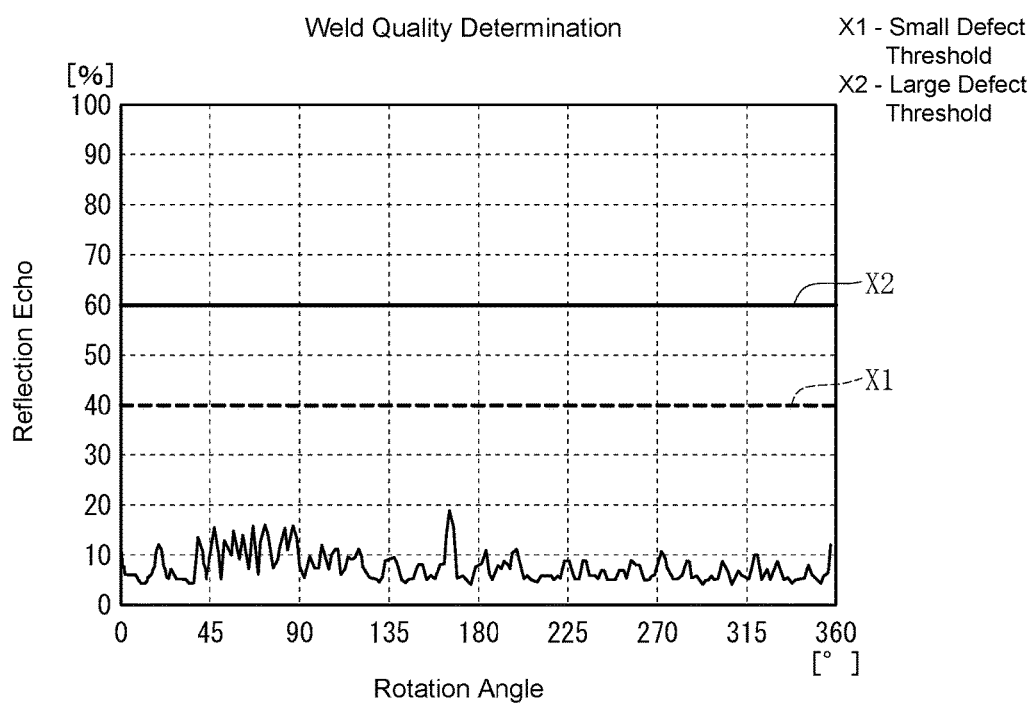
FIG. 17 is an explanatory graph for showing an overview of a quality determination program for a detection result of a defect of a welded portion.
Figure 18:
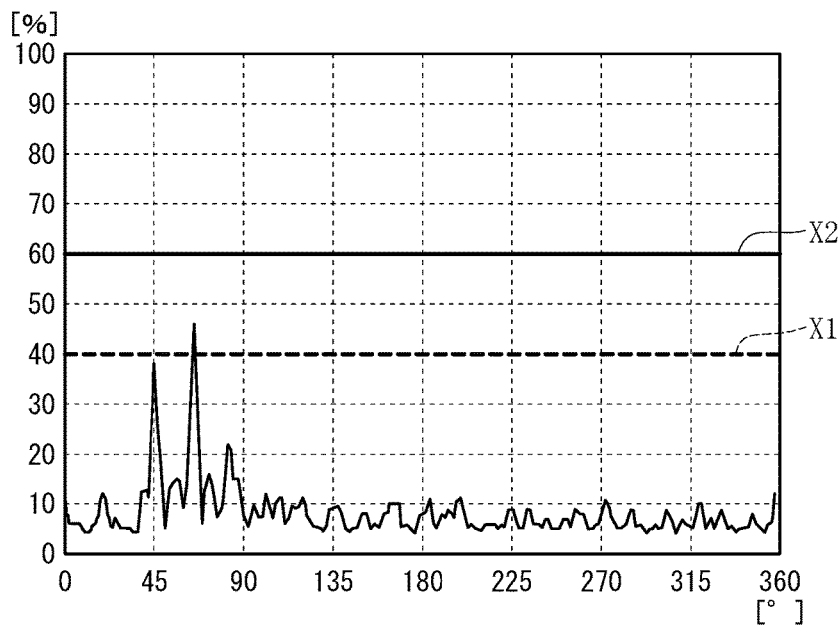
FIG. 18 is an explanatory graph for showing an overview of the quality determination program for a detection result of a defect of the welded portion.
Figure 19:
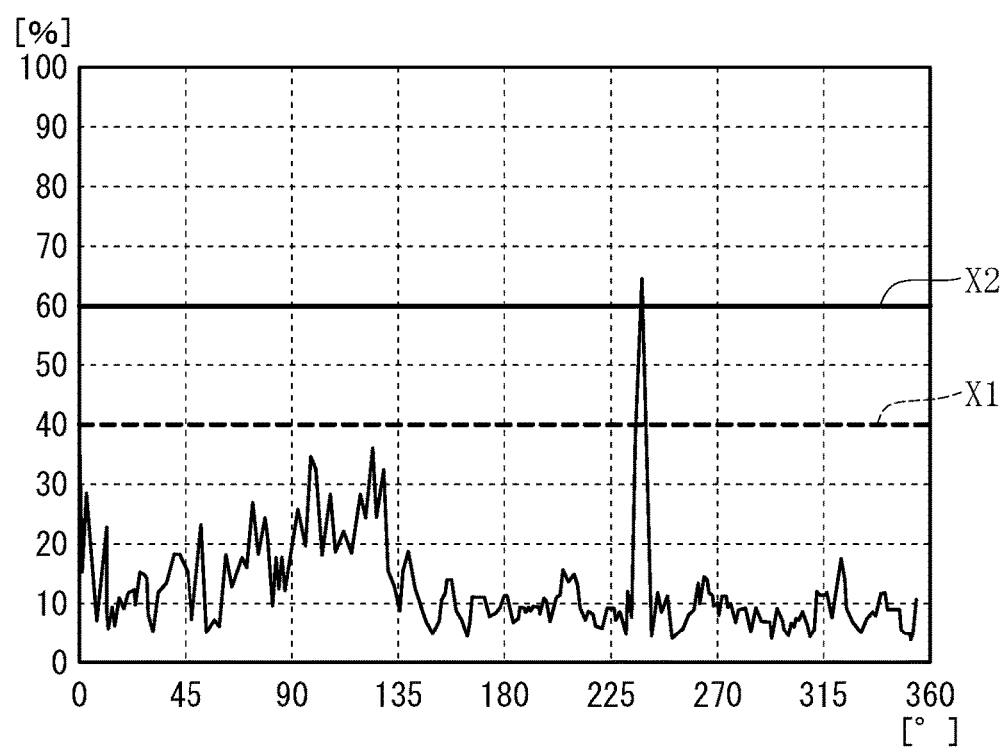
FIG. 19 is an explanatory graph for showing an overview of the quality determination program for a detection result of a defect of the welded portion.

Following the above description of the overview of the manufacturing steps (processing steps) of the first embodiment, the features of the first embodiment, that is, the ultrasonic flaw detection-inspection step for the welded portion is described with reference to FIG. 8 to FIG. 19. FIG. 8 is a front view for illustrating an overview of an ultrasonic flaw detection-inspection apparatus. FIG. 9 is a plan view, and FIG. 10 is a right side view. In each of the states illustrated in FIG. 8 to FIG. 10, the outer joint member after welding is placed in the ultrasonic flaw detection-inspection apparatus. FIG. 11 is a right side view for illustrating a state in which the centering of the outer joint member is performed by upper and lower center hole guides. FIG. 12 is a plan view for illustrating a state in which a probe has moved to a flaw detection position after the centering of FIG. 11. FIG. 13 is a partial plan view for illustrating a positional relationship between the probe and the outer joint member. FIG. 14 to FIG. 16 are views for illustrating an overview of states of inspection by ultrasonic flaw detection methods. FIG. 17 to FIG. 19 are explanatory graphs for showing an overview of a quality determination program for a detection result of a defect of the welded portion.

As illustrated in FIG. 8 to FIG. 10, an ultrasonic flaw detection-inspection apparatus 120 mainly comprises a water bath 122 mounted to a base 121, a workpiece support 123, a lifting device 147 for the workpiece support 123, an upper center hole guide 124, a drive positioning device 128 for the upper center hole guide 124, a lower center hole guide 126, a rotary drive device 125 configured to rotate an intermediate product 11' (hereinafter also referred to as "workpiece 11'") of the outer joint member 11, and a drive positioning device 161 for the probe 160. An outer frame of the ultrasonic flaw detection-inspection apparatus 120 is an assembly of a frame 133, and the base 121 is mounted to the frame 133.

As illustrated in FIG. 10, the drive positioning device 128 for the upper center hole guide 124 comprises a vertical-direction drive positioning device 129 and a horizontal-direction drive positioning device 130. The horizontal-direction drive positioning device 130 is provided to an upper end portion of a support column 132 fixed to the base 121. The horizontal-direction drive positioning device 130 mainly comprises linear-motion bearings 135, a moving member 136, and a drive cylinder 137. The linear-motion bearings 135 are mounted to the upper end portion of the support column 132, and comprise rails 134 and linear guides 139. The drive cylinder 137 is coupled to the moving member 136. The moving member 136 is driven and positioned in the horizontal direction by the drive cylinder 137.

The vertical-direction drive positioning device 129 is provided to a support member 138 mounted to the moving member 136 of the horizontal-direction drive positioning device 130. The vertical-direction drive positioning device 129 mainly comprises the upper center hole guide 124, a drive cylinder 142, and a linear-motion bearing 140. The drive cylinder 142 is coupled to the upper center hole guide 124. The linear-motion bearing 140 comprises a rail 139 and linear guides 141 mounted to the support member 138. The upper center hole guide 124 is driven and positioned in the vertical direction by the drive cylinder 142. A center 124a is rotatably mounted to the upper center hole guide 124 through intermediation of a rolling bearing or the like (not shown). A set position of the drive cylinder 142 in the vertical direction is adjustable by a suitable mechanism such as a feed-screw mechanism (not shown) in accordance with a product number and an axial dimension of the workpiece 11'.

The lower center hole guide 126 is mounted to a rotary shaft 143a of a rotary support member 143 mounted to the base 121. The rotary shaft 143a is driven to rotate by a servomotor 145 mounted to a side plate 144. The rotary shaft 143a has an engagement piece 146 which is engaged with the track grooves 30 (see FIG. 2a) of the workpiece 11' to transmit a rotational drive force. A center 126a of the lower center hole guide 126 is rotatable, but a position in the vertical direction is fixed.

The workpiece support 123 is mounted to the lifting device 147. The lifting device 147 comprises a linear-motion bearing 149, a moving member 151, and a drive cylinder 152. The linear-motion bearing 149 comprises a rail 148 and linear guides 150 mounted to a side surface of the support column 132. The drive cylinder 152 is coupled to the moving member 151. The workpiece support 123 is slightly movable in the vertical direction by the lifting device 147.

The drive positioning device 161 for the probe 160 is described with reference to FIG. 8 and FIG. 9. As illustrated in FIG. 8, a fixed member 155 is provided to the base 121, and a drive cylinder (electric cylinder) 156 is mounted between the fixed member 155 and an upper portion of the frame 133. The fixed member 155 comprises a plate-shaped member 155a, and a rail 157 indicated by the two-dot chain lines is mounted to a back surface of the plate-shaped member 155a. A base member 159 of the drive positioning device 161 for the probe 160 is arranged opposed to the plate-shaped member 155a. A linear guide 158 is mounted to the base member 159 so that the base member 159 is movable along the rail 157. The base member 159 is coupled to the drive cylinder 156. With this configuration, the base member 159 is driven and positioned in the vertical direction, that is, in the Z-axis direction.

Rails 162 are mounted on the upper surface of the base member 159 in the right-and-left direction in FIG. 8, and a movable base 164 is provided through intermediation of linear guides 163. The movable base 164 is coupled to the drive cylinder (electric cylinder) 165 mounted to the upper surface of the base member 159. With this configuration, the movable base 164 is driven and positioned in the right-and-left direction in FIG. 8, that is, in the X-axis direction.

The movable base 164 comprises a mounting portion 164a on an upper side, and a drive cylinder (electric cylinder) 166 is mounted to the mounting portion 164a. An arm member 167 of the probe 160 is mounted to the drive cylinder 166. With this configuration, the arm member 167 is driven and positioned in the front-and-rear direction of FIG. 8, that is, in the Y-axis direction illustrated in FIG. 9.

As described above, the drive cylinders in the X-axis direction, the Y-axis direction, and the Z-axis direction are electric cylinders of an electric ball-screw type. Therefore, positioning with high accuracy can be performed.

In the illustrations in FIG. 8, FIG. 10, and FIG. 11, for easy understanding of a state of arrangement of the members, a side wall of the water bath 122 on the near side in FIG. 8, FIG. 10, and FIG. 11 is cut, and a water surface is omitted. In the ultrasonic flaw detection-inspection apparatus 120 of the first embodiment, a flaw portion of the workpiece 11', the workpiece support 123, a part of the moving member 151, the lower center hole guide 126, a part of the rotary support member 143, and parts of the probe 160 and the arm member 167 are arranged in the water bath 122 so as to be soaked in water.

Detailed description is made of the arm member 167 of the probe 160 with reference to FIG. 13. The probe 160 is mounted to a lower portion of the arm member 167. The probe 160 is mounted to a gear 168 through intermediation of a holder 172. An electric rotary actuator 169 is mounted to an upper portion of the arm member 167, and a gear 170 having the same number of teeth and modules as those of the gear 168 is mounted to the electric rotary actuator 169. A rack 171 is in mesh with the gear 168 and the gear 170. Therefore, a rotary motion of the electric rotary actuator 169 is transmitted from the gear 170 to the rack 171 and the gear 168, and a rotation angle of the electric rotary actuator 169 and a rotation angle of the probe 160 are equal to each other. With this configuration, an incident angle of the probe 160 can be set variable. Backlash of the rack 171 and the gears 168 and 170 is suppressed, and hence the electric rotary actuator 169 and the probe 160 rotate in synchronization with each other. An original point of the rotation angle of the electric rotary actuator 169 is determined in the following manner. A bottom side of the holder 172 for the probe 160 is brought into abutment against an angle checking jig (not shown) to be in a horizontal state, and a rotation angle of the electric rotary actuator 169 in this state is set to the original point. The rotation angle of the electric rotary actuator 169 with respect to the original point is represented by R. In the first embodiment, the transmission mechanism using the rack 171 and the gears 168 and 170 is exemplified. However, the transmission mechanism is not limited thereto. A transmission mechanism using, for example, a timing belt and pulleys may also be used.

Next, description is made of an operation of the ultrasonic flaw detection-inspection apparatus 120 and an ultrasonic flaw detection-inspection step S6k. First, with reference to FIG. 8 to FIG. 10, description is made of a state before the workpiece 11' after welding is placed. Water is supplied to the water bath 122. As illustrated in FIG. 10, the upper center hole guide 124 waits at a position retreated in the horizontal direction by the drive cylinder 137 of the horizontal-direction drive positioning device 130. At this time, the upper center hole guide 124 is at a position retreated upward by an appropriate distance by the drive cylinder 142 of the vertical-direction drive positioning device 129 so as to prevent interference with a shaft end of the workpiece 11'. The workpiece support 123 is positioned on an upper side by an appropriate distance by the drive cylinder 152 of the lifting device 147 so that the center 126a of the lower center hole guide 126 is positioned on the near side of a position at which the center 126a faces a center hole of the workpiece 11'.

As illustrated in FIG. 8 and FIG. 9, the arm member 167 of the probe 160 waits at a position on the left-far side of the water bath 122 (see FIG. 9) by the Z-axis-direction drive cylinder 156, the Y-axis-direction drive cylinder 166, and the X-axis-direction drive cylinder 165 of the drive positioning device 161 for the probe 160. This position is set as an original position and serves as an original point for a program described later.

In the above-mentioned initial state, the workpiece 11' after welding is placed on the workpiece support 123 by a loader (not shown). FIG. 8 to FIG. 10 are each an illustration of a state in which the workpiece 11' is placed on the workpiece support 123. Under the state in which the workpiece 11' is placed on the workpiece support 123, the center 126a of the lower center hole guide 126 is at a position on the near side of the position at which the center 126 faces the center hole of the workpiece 11'.

After that, as illustrated in FIG. 11, the upper center hole guide 124 is caused to advance by the drive cylinder 137 of the horizontal-direction drive positioning device 130, and is positioned at a position in the horizontal direction of the upper center hole of the workpiece 11'. Subsequently, the upper center hole guide 124 is caused to advance to a lower side by the drive cylinder 142 of the vertical-direction drive positioning device 129, and is fitted to the upper center hole of the workpiece 11'. Subsequently, as the upper center hole guide 124 is caused to advance, the workpiece support 123 is lifted down. As a result, the center 126*a* of the lower center hole guide 126 is fitted to the lower center hole of the workpiece 11', and the centering of the workpiece 11' is performed.

After that, the Z-axis-direction drive cylinder 156 of the drive positioning device 161 for the probe 160 causes the probe 160 to advance in the Z-axis direction (vertical direction) to a position corresponding to a flaw detection position. Further, the Y-axis-direction drive cylinder 166 causes the probe 160 to advance in the Y-axis direction (horizontal direction) to a position corresponding to the flaw detection position. Finally, the X-axis-direction drive cylinder 165 causes the probe 160 to advance in the X-axis direction (horizontal direction). As a result, as illustrated in FIG. 12 and FIG. 13, the probe 160 is positioned at the flaw detection position. In the first embodiment, description is made of the example in which the probe 160 is driven and positioned in the order of the Z-axis direction, the Y-axis direction, and the X-axis direction. However, the order is not limited to the above-mentioned order, and may be suitably changed.

After the probe 160 is positioned at the flaw detection position, the ultrasonic flaw detection-inspection is performed. A defect of the welded portion 49 is random in shape and orientation. However, the ultrasonic flaw detection-inspection in the first embodiment has a feature in that the welded portion 49 is inspected by a plurality of ultrasonic flaw detection methods with one probe 160, thereby being capable of performing defect detection for the welded portion 49 of the outer joint member 11 of the constant velocity universal joint 10 being a mass-produced product for automobiles and the like with high detection accuracy and in a wide detection range and also at the level of enabling industrial production.

Figure 14A:
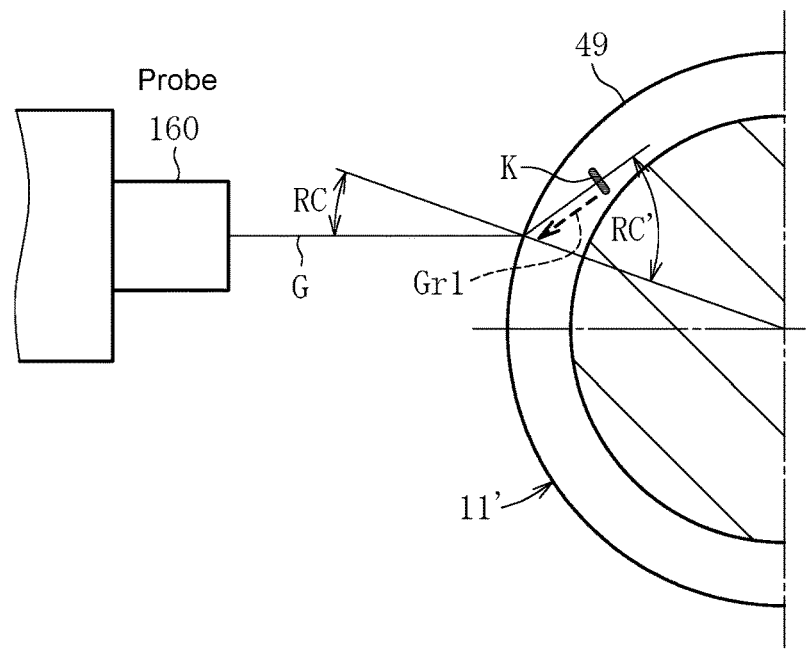
FIG. 14a is an illustration of a state of inspection by a circumferential angle beam flaw detection method, and is a partial cross-sectional view taken along the line I-I of FIG. 14b.
Figure 14B:
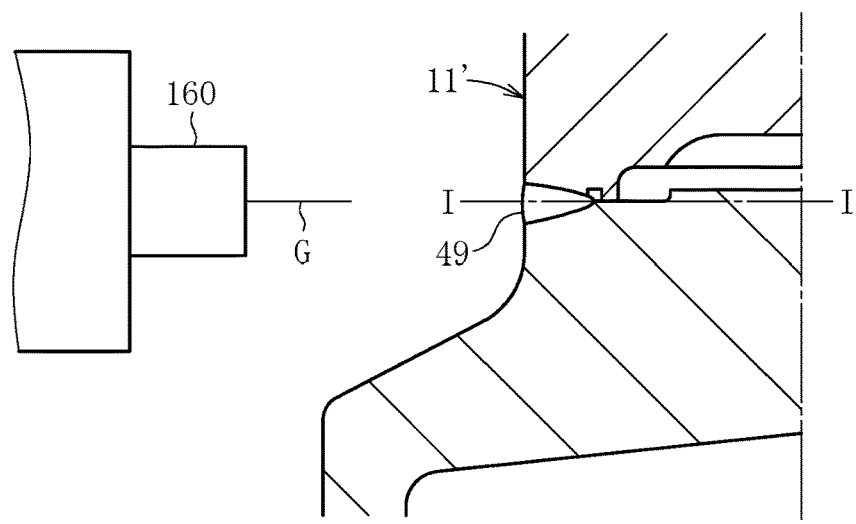
FIG. 14b is an illustration of a state of inspection by the circumferential angle beam flaw detection method, and is a partial vertical sectional view of the outer joint member.

First, inspection by the circumferential angle beam flaw detection method is performed. A state of the inspection is described with reference to FIG. 14. FIG. 14*a* is a partial cross-sectional view taken along the line I-I of FIG. 14*b*. FIG. 14*b* is a partial vertical sectional view of the workpiece 11'. For simplification of the drawings, hatching of the welded portion 49 is omitted. This similarly applies to FIG. 15 and FIG. 16 described later. In the circumferential angle beam flaw detection method, an axis of a transmission pulse G of the probe 160 is perpendicular to an axis of the workpiece 11' and is parallel to the vertical cross section of FIG. 14*b*. At this time, the rotation angle R of the electric rotary actuator 169 which changes the axis of the transmission pulse G of the probe 160 is 0°. However, in a case of a probe of a type with an inclined axis of the transmission pulse, the rotation angle R of the electric rotary actuator is adjusted by the degree of inclination to cause the axis of the transmission pulse G to be perpendicular to the axis of the workpiece 11' and be parallel to the vertical cross section of FIG. 14*b*. As illustrated in FIG. 14*a*, the probe 160 is positioned by being offset in the Y-axis direction. Therefore, an incident angle corresponding to a circumferential inclination angle RC is formed, and a refraction angle RC' is given.

The transmission pulse G is successively transmitted from the probe 160. The servomotor 145 reversely rotates to a suitable rotation angle, and thereafter forwardly rotates to receive by one step a reflection echo Gr1 for one rotation (360°) being associated with a phase angle as a first step with a phase angle of 0° as an original point in a constant velocity rotation state. The defect K of the welded portion 49 is random in shape and orientation. However, as illustrated in FIG. 14*a*, the defect K which is substantially perpendicular to the refraction angle RC' is detected. Next, as a second step, a position in the Z-axis direction is shifted (positions in the X-axis direction and the Y-axis direction are not changed, and this applies to the next third step), and similarly to the first step, the servomotor 145 rotates with the phase angle 0° as an original point, and receives the reflection echo Gr1 for one rotation (360°) being associated with the phase angle. As a third step, the position in the Z-axis direction is further shifted, and similarly to the previous step, the servomotor 145 receives the reflection echo Gr1 for one rotation (360°) being associated with the phase angle. The positions in the X-axis direction, the Y-axis direction, and the Z-axis direction are controlled by a program.

Figure 15A:
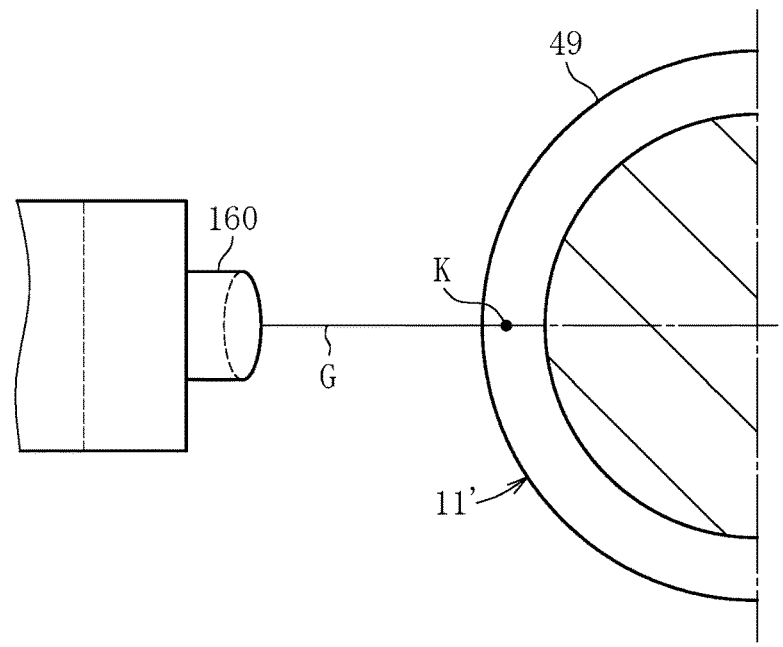
FIG. 15a is an illustration of a state of inspection by an axial angle beam flaw detection method, and is a partial cross-sectional view taken along the line I-I of FIG. 15b.
Figure 15B:
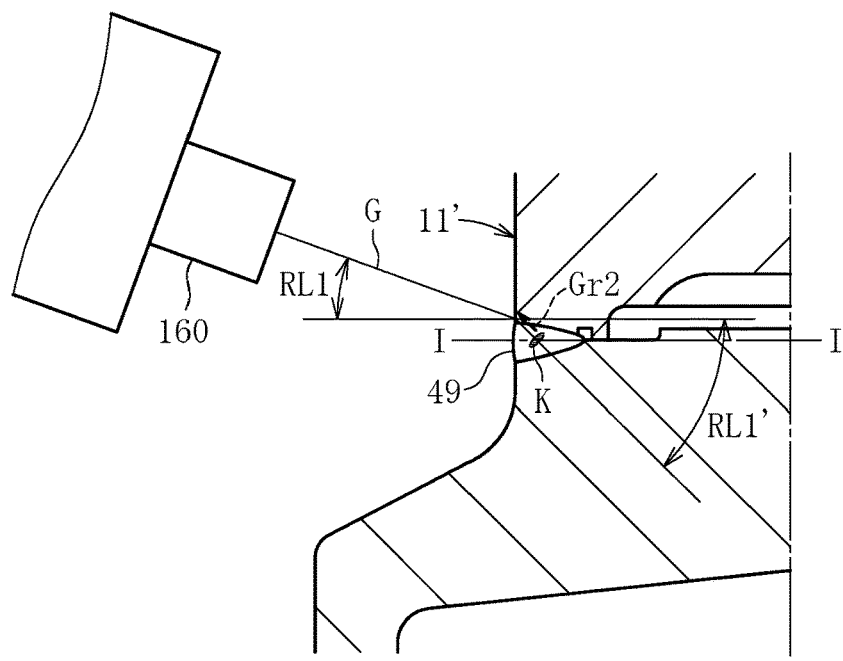
FIG. 15b is an illustration of a state of inspection by the axial angle beam flaw detection method, and is a partial vertical sectional view of the outer joint member.

Next, the inspection is performed by the axial angle beam flaw detection method which is a different ultrasonic flaw detection method. A state of this inspection is described with reference to FIG. 15. FIG. 15*a* is a partial cross-sectional view taken along the line I-I of FIG. 15*b*. FIG. 15*b* is a partial vertical sectional view of the workpiece 11'. In the axial angle beam flaw detection method, a rotation angle R is given to the electric rotary actuator 169. As a result, an axial inclination angle RL1 (for example, 19°) being an incident angle is given, and a refraction angle RL1' is given. This axial angle beam flaw detection method is referred to as a first axial angle beam flaw detection method. As described above, the axial inclination angle RL1 is given by the rotation angle R of the electric rotary actuator 169 in FIG. 13, and the electric rotary actuator 169 is controlled by a program.

Also in the first axial angle beam flaw detection method, the transmission pulse G is successively transmitted from the probe 160. Similarly to the above-mentioned circumferential angle beam flaw detection method, the servomotor 145 rotates with the phase angle 0° as an original point, and as a fourth step, receives a reflection pulse Gr2 for one rotation (360°) being associated with the phase angle. The defect K of the welded portion 49 is random in shape and orientation. However, as illustrated in FIG. 15*a*, the defect K which is substantially perpendicular to the refraction angle RL1' is detected. Next, in a fifth step and a sixth step, positions in the Z-axis direction are sequentially shifted (positions in the X-axis direction and the Y-axis direction are not changed), and the servomotor 145 receives the reflection pulse Gr2 for one rotation (360°) for each step being associated with the phase angle.

Next, the rotation angle R of the electric rotary actuator 169 is changed, and the inspection is performed by a second axial angle beam flaw detection method. A state of this inspection is described with reference to FIG. 16. FIG. 16*a* is a partial cross-sectional view taken along the line I-I of FIG. 16*b*. FIG. 16*b* is a partial vertical sectional view of the workpiece 11'. In the second axial angle beam flaw detection method, an axial inclination angle RL2 (for example, 24°) is given as an incident angle, and a refraction angle RL2' is given.

Similarly to the first axial axial angle beam flaw detection method, in the second axial angle beam flaw detection method, a reflection echo Gr3 is received by flaw detection of seventh to ninth steps.

The plurality of flaw detection methods comprising the circumferential angle beam flaw detection method and the axial angle beam flaw detection method are adaptable to various orientations of the defect K of the welded portion 49. Further, flaw detection methods have the following features. The circumferential angle beam flaw detection method is capable of performing detection in a wide range in the radial direction from the surface of the welded portion 49 to an inner diameter portion. Meanwhile, the axial angle beam flaw detection method is basically difficult to perform detection with respect to a vicinity of the surface of the welded portion 49. However, the refraction angle in the case of the first axial angle beam flaw detection method (incident angle RL1=19°) is smaller than the refraction angle in the case of the second axial angle beam flaw detection method (RL2=24°). Therefore, the first axial angle beam flaw detection method can easily perform detection with respect to the region from the surface of the welded portion 49 to the radially inner side, and the second axial angle beam flaw detection method can easily perform detection with respect to the region on a side closer to the surface than the first axial flaw detection method. In this regard, in the first embodiment, the flaw detection for the welded portion can be secured with high detection accuracy and a wide detection range.

The orders of the circumferential angle beam flaw detection method and the first and second axial angle beam flaw detection methods described above may suitably be changed.

An example of command values of the program for each of the flaw detection methods described above is collectively shown in Table 1. Such flaw detection program is set in advance for each product number. An operator can select a flaw detection program set for each product number so that the inspection can automatically be performed after the workpiece 11' is provided. Thus, the control of positions and angles of the probe 160 based on command values of the program enables the inspection to be applied to complicated shapes of workpieces (outer joint members) and to outer joint members having different product numbers. At the same time, adjustment of setup for equipment can easily be performed, thereby being capable of securing repeatability of inspection.

nation program for a detection result of a defect of the welded portion. In the graph shown in FIG. 17, a reflection echo being a base without a defect (hereinafter referred to as "base echo") is shown. The threshold value X1 is set to a twofold value of a maximum value of the base echo (20%) as a reference, and the threshold value X2 is set to a threefold value of the maximum value of the base echo.

The reflection echo provides one data piece per 1°, and hence three hundred and sixty data pieces are provided for one rotation. The threshold value X1 was set for determination of quality in a case in which a small defect is detected. When ten or more data pieces of the reflection echo exceeding the threshold value X1 are detected in one rotation (360°) of the welded portion, it is determined that a product has a poor quality. In the data of the reflection echo shown in FIG. 18, two data pieces exceed the threshold value X1 in one rotation of the welded portion, and hence it is determined that a product has a good quality.

The threshold value X2 was set for determination of a quality in a case in which a large defect is detected. When at least one data piece of the reflection echo exceeding the threshold value X2 is detected for one rotation (360°) of the welded portion, it is determined that a product has a poor quality. In the data of the reflection echo shown in FIG. 19, two data pieces exceed the threshold value X1, and hence it is determined that the product has a good quality in terms of the threshold value X1. However, one data piece exceeds the threshold value X2, and hence it is eventually determined that the product has a poor quality.

As described above, when determination of poor quality is given based on any one of the threshold values X1 and X2, the workpiece 11' is determined as having a poor quality. The inspection can automatically be performed by performing the quality determination based on the data of the reflection echo with the threshold values X1 and X2. However, deter-

TABLE 1

| Step | Position in X-axis Direction | Position in Y-axis Direction | Position in Z-axis Direction | Rotation Angle R of Robot Rotary | Remarks |
| --- | --- | --- | --- | --- | --- |
| 1 | 3.0 | 5.0 | 2.0 | 0 | Circumferential |
| 2 | 3.0 | 5.0 | 2.5 | 0 | Angle Beam Flaw |
| 3 | 3.0 | 5.0 | 3.0 | 0 | Detection Method |
| 4 | 3.5 | 5.0 | 3.0 | 19 | Axial Angle Beam |
| 5 | 3.5 | 5.0 | 3.5 | 19 | Flaw Detection |
| 6 | 3.5 | 5.0 | 4.0 | 19 | Method Incident Angle 19° |
| 7 | 4.5 | 5.0 | 3.0 | 24 | Axial Angle Beam |
| 8 | 4.5 | 5.0 | 3.5 | 24 | Flaw Detection |
| 9 | 4.5 | 5.0 | 4.0 | 24 | Method Incident Angle 24° |

The example of the steps and command values of the program for each of the flaw detection methods described above is not limited to the example shown in Table 1. In the example shown in Table 1, the example using the three flaw detection methods is shown. However, depending on the workpiece 11' subjected to inspection, the flaw detection method may be suitably changed to two flaw detection methods or four or more flaw detection methods. That is, the number of the flaw detection methods may be any number as long as the defect detection can secure high detection accuracy and a wide detection range by a plurality of different flaw detection methods with one probe.

Next, with reference to FIG. 17 to FIG. 19, description is made of an overview of an example of a quality determimination criteria for the quality determination may be suitably adjusted in accordance with an actual state of the workpiece 11'.

After the flaw detection inspection is terminated, the probe 160 returns to the waiting position illustrated in FIG. 8 to FIG. 10, and the workpiece 11' is conveyed by the loader (not shown) from the ultrasonic flaw detection device 120. In such a manner, the inspection for the workpiece 11' is sequentially repeated.

As described above, the ultrasonic flaw detection-inspection apparatus 120 of the first embodiment mainly comprises the water bath 122 mounted to the base 121, the workpiece support 123, the lifting device 147 for the workpiece support 123, the upper center hole guide 124, the drive positioning device 128 for the upper center hole guide 124, the lower center hole guide 126, the rotary drive device 125 configured to rotate the intermediate product 11' (hereinafter also referred to as "workpiece 11'") of the outer joint member 11, and the drive positioning device 161 for the probe 160. With this configuration, the operations of supply of water, drainage of water, conveyance of the workpiece 11' to the flaw detection inspection apparatus 120, flaw detection inspection, and conveyance of the workpiece 11' from the flaw detection inspection apparatus 120 can be performed in conjunction, thereby being capable of automating the ultrasonic flaw detection-inspection. Thus, the welded portion 49 is inspected by a plurality of ultrasonic flaw detection methods with one probe 160, thereby being capable of performing defect detection for the welded portion 49 with high detection accuracy and in a wide detection range and also at the level of enabling industrial production. In addition to the above-mentioned feature, the accuracy, the operability, and the efficiency in the inspection can be enhanced, and hence the flaw detection inspection apparatus 120 is suitable for inspection of a welded portion of an outer joint member of a constant velocity universal joint being a mass-produced product.

Further, the outer diameter B1 of the joining end surface 50 of the cup member 12a of the first embodiment is set to an equal dimension for each joint size. Also with this base configuration, in the ultrasonic flaw-detection inspection, setup operations with respect to the outer joint members 11 having the different product numbers are simplified. Thus, the efficiency in the inspection can be further enhanced. Still further, flaw detection is performed under water, and hence ultrasonic waves are satisfactorily propagated. Thus, inspection can be performed with higher accuracy.

Figure 20:
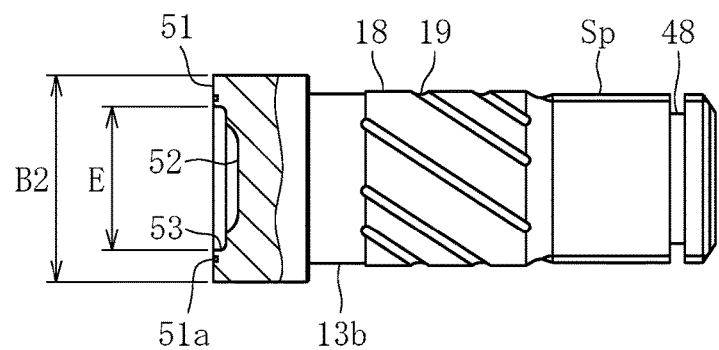
FIG. 20 is a front view for illustrating a shaft member assigned with a product number different from that of the shaft member of FIG. 5c.
Figure 21:
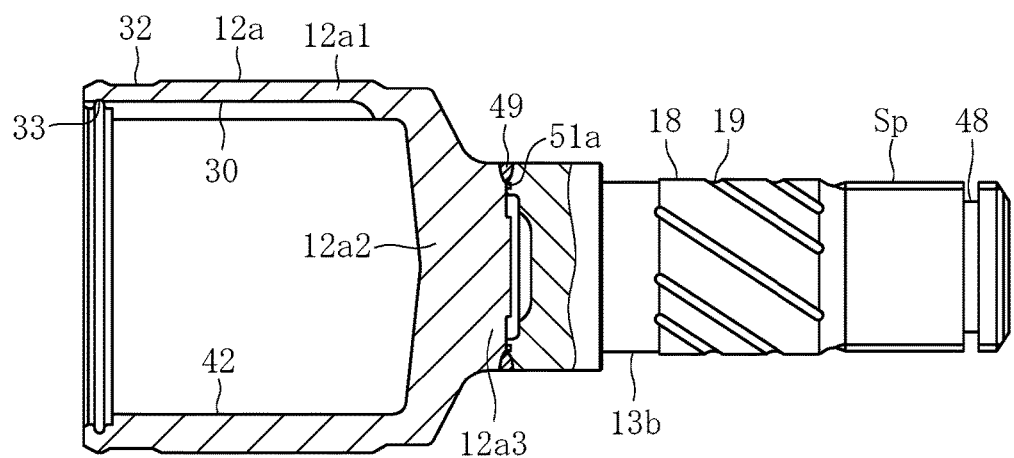
FIG. 21 is a partial vertical sectional view for illustrating an outer joint member that is manufactured using the shaft member of FIG. 20.

Next, to summarize the manufacturing concept, standardization of a product type of the cup member is additionally described while exemplifying a shaft member having a product number different from that of the above-mentioned shaft member 13a of the long stem type illustrated in FIG. 5. A shaft member 13b illustrated in FIG. 20 and FIG. 21 is used as a general stem type on the inboard side. The shaft member 13b has the joining end surface 51 to be brought into abutment against the joining end surface 50 (see FIG. 4b) of the bottom portion 12a2 (projecting portion 12a3) of the cup member 12a. The outer diameter B2 and the inner diameter E of the joining end surface 51 are set to the equal dimensions to the outer diameter B and the inner diameter E of the joining end surface 51 of the shaft member 13a of the long stem type illustrated in FIG. 5c.

The shaft member 13b is used as the general stem type on the inboard side. Accordingly, the shaft member 13b comprises a shaft section with a small length, and a sliding bearing surface 18 formed on an axial center portion thereof, and a plurality of oil grooves 19 are formed in the sliding bearing surface 18. The spline Sp and a snap ring groove 48 are formed in an end portion of the shaft member 13b on the side opposite to the cup member 12a side. As described above, even when there are differences in types, such as the general length stem type and the long stem type, and shaft diameters and outer peripheral shapes vary in each vehicle type, the outer diameter B of the joining end surface 51 of the shaft members 13a and 13b is set to an equal dimension.

The outer diameters B1 of the joining end surface 50 of the cup member 12a and the joining end surface 51 of the shaft members 13a and 13b are set to an equal dimension for each joint size. Thus, the cup member prepared for common use for each joint size, and the shaft member having a variety of specifications of the shaft section for each vehicle type can be prepared in a state before heat treatment. Further, the intermediate component of each of the cup member 12a and the shaft members 13a and 13b can be assigned with a product number for management. Even when standardizing product types of the cup member 12a, various types of the outer joint members 11 satisfying requirements can be produced quickly through combination of the cup member 12a and the shaft members 13a and 13b each having a variety of specifications of the shaft section for each vehicle type. Therefore, standardization of a product type of the cup member 12a can reduce cost and alleviate a burden of production management.

The standardization of the product type of the cup member is described above by taking the differences in types, such as the general length stem type and the long stem type, as an example for easy understanding, but the present invention is not limited thereto. The same applies to standardization of the product type of the cup member for shaft members having a variety of specifications of the shaft section for each vehicle type among the general length stem types, and for shaft members having a variety of specifications of the shaft section for each vehicle type among the long stem types.

Figure 22:
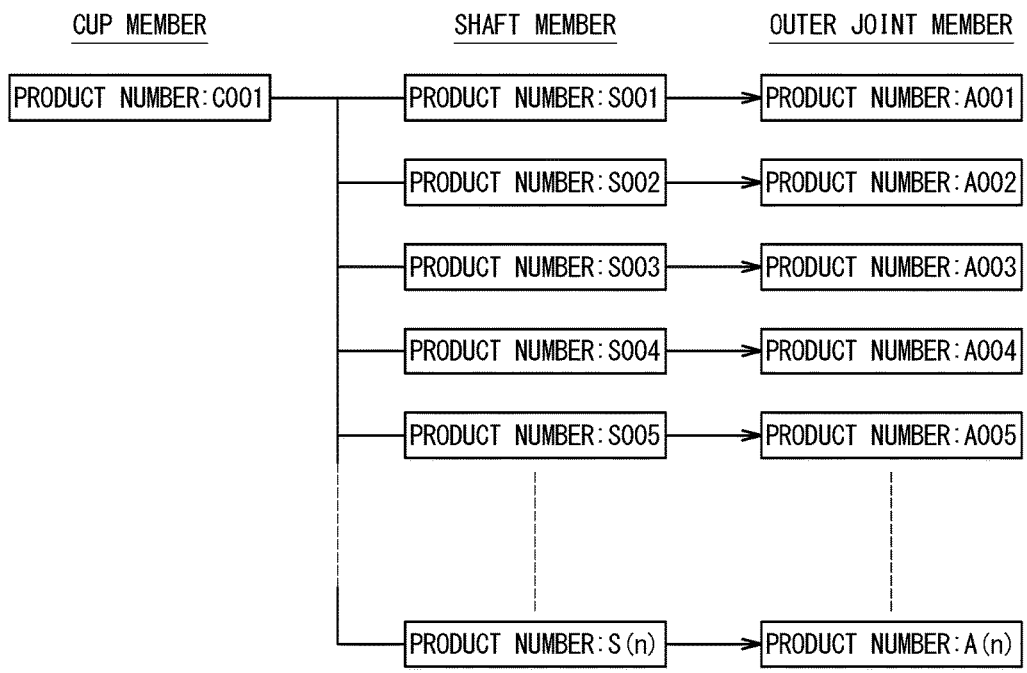
FIG. 22 is a diagram for illustrating an example of standardization of a product type of the cup member.

As a summary of the above description, FIG. 22 is a diagram for illustrating an example of standardization of a product type of the cup member according to the first embodiment. As illustrated in FIG. 22, the cup member is prepared for common use for one joint size, and is assigned with, for example, a product number C001 for management. In contrast, the shaft member has a variety of specifications of the shaft section for each vehicle type, and is assigned with, for example, a product number S001, S002, or S(n) for management. For example, when the cup member assigned with the product number C001 and the shaft member assigned with the product number S001 are combined and welded to each other, the outer joint member assigned with a product number A001 can be produced. Thus, owing to standardization of a product type of the cup member, it is possible to reduce cost and to alleviate a burden of production management. In the standardization of a product type, the cup member is not limited to one type for one joint size, that is, not limited to one type assigned with a single product number. For example, the cup member comprises cup members of a plurality of types (assigned with a plurality of product numbers, respectively) that are prepared for one joint size based on different specifications of a maximum operating angle, and are each prepared so that the outer diameter B of the joining end surface of each of those cup members has an equal dimension.

Figure 23:
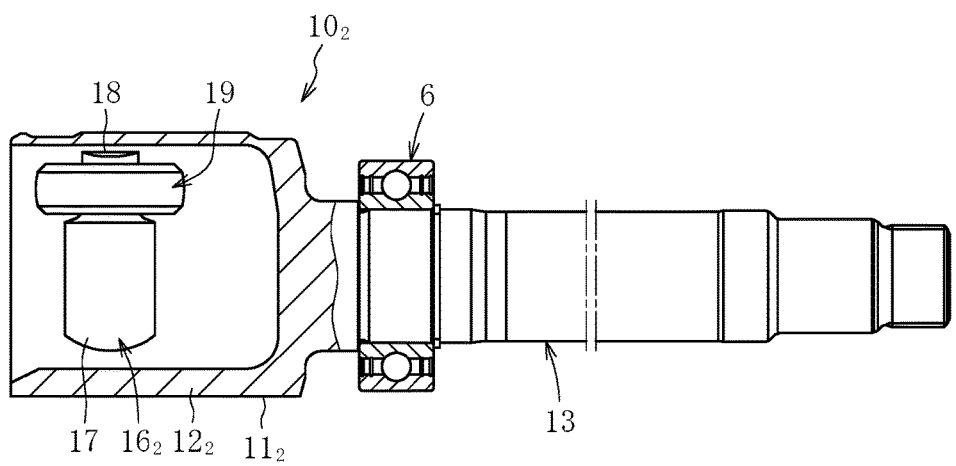
FIG. 23 is a partial vertical sectional view for illustrating a constant velocity universal joint of a different type, which is manufactured based on the first embodiment.

Next, with reference to FIG. 23 and FIG. 24, description is made of a constant velocity universal joint and an outer joint member which are of types different from those of the constant velocity universal joint and the outer joint member of FIG. 1 and FIG. 2a which are manufactured based on the manufacturing method according to the first embodiment of the present invention. With regard to the constant velocity universal joint and the outer joint member, the parts having the same functions as those of the constant velocity universal joint and the outer joint member illustrated in FIG. 1 and FIG. 2a are denoted by the same reference symbols (except for subscripts), and only the main points are described.

A plunging type constant velocity universal joint $10_2$ illustrated in FIG. 23 is a tripod type constant velocity universal joint (TJ), and comprises an outer joint member $11_2$ comprising a cup section $12_2$ and the long stem section 13 that extends from a bottom portion of the cup section $12_2$ in the axial direction, an inner joint member $16_2$ housed along an inner periphery of the cup section $12_2$ of the outer joint member $11_2$, and rollers 19 serving as torque transmitting elements that are arranged between the outer joint member $11_2$ and the inner joint member $16_2$. The inner joint member $16_2$ comprises a tripod member 17 comprising three equiangular leg shafts 18 on which the rollers 19 are externally fitted.

The inner ring of the support bearing 6 is fixed to the outer peripheral surface of the long stem section 13, and the outer ring of the support bearing 6 is fixed to the transmission case with the bracket (not shown). The outer joint member $11_2$ is supported by the support bearing 6 in a freely rotatable manner, and thus the vibration of the outer joint member $11_2$ during driving or the like is prevented as much as possible.

Figure 24B:
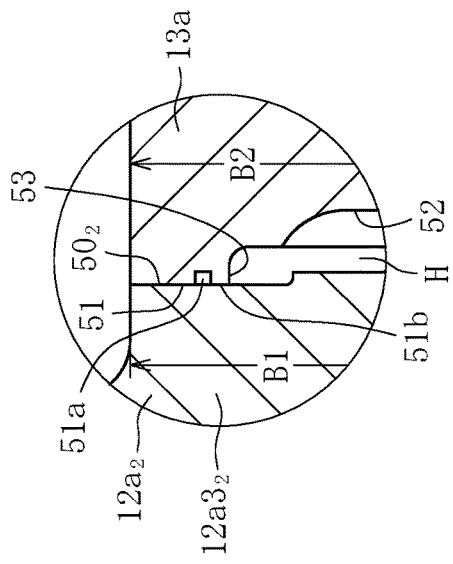
FIG. 24b is an enlarged view for illustrating a shape of the portion A of FIG. 24a before welding.
Figure 24A:
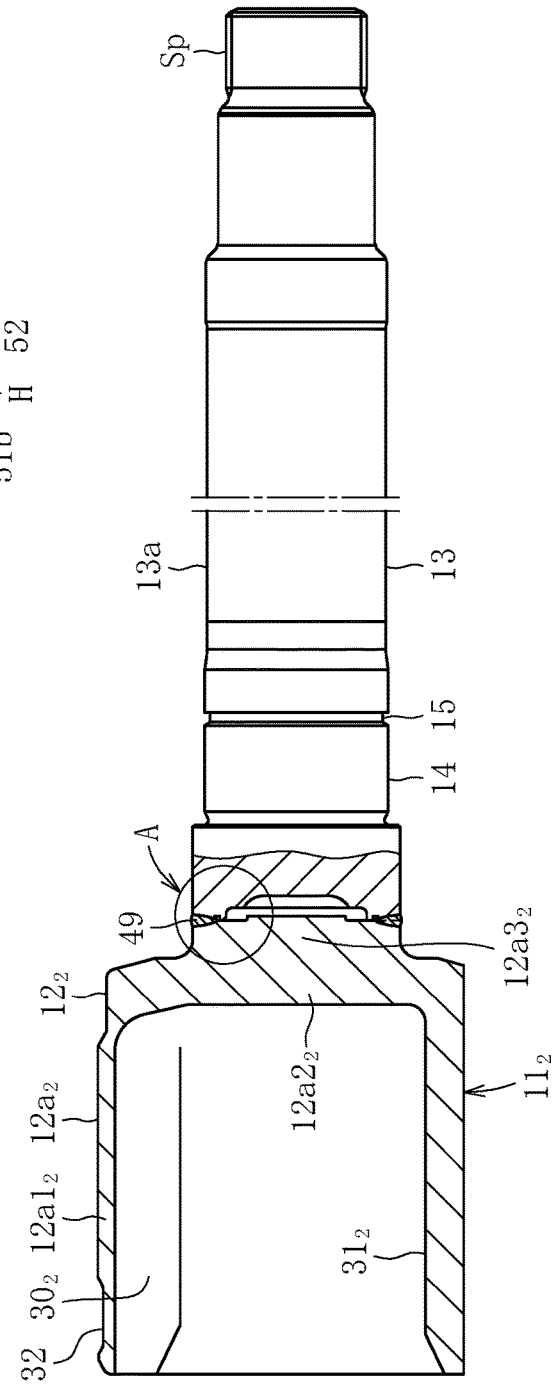
FIG. 24a is an enlarged partial vertical sectional view for illustrating the outer joint member of FIG. 23.

FIG. 24a is a partial vertical sectional view for illustrating the outer joint member $11_2$. As illustrated in FIG. 24a, the outer joint member $11_2$ comprises a bottomed cylindrical cup section $12_2$ that is opened at one end and has inner peripheral surfaces $31_2$ and the track grooves $30_2$, on which the rollers 19 (see FIG. 23) are caused to roll, formed at three equiangular positions on an inner peripheral surface of the cup section $12_2$, and the long stem section 13 that extends from a bottom portion of the cup section $12_2$ in the axial direction and comprises the spline Sp serving as the torque transmitting coupling portion formed at the outer periphery of the end portion on the opposite side to the cup section $12_2$ side. The outer joint member $11_2$ is formed by welding the cup member $12a_2$ and the shaft member 13a to each other.

As illustrated in FIG. 24a, the cup member $12a_2$ is an integrally-formed product having a cylindrical portion $12a1_2$ and a bottom portion $12a2_2$. The cylindrical portion $12a1_2$ has the track grooves $30_2$ and the inner peripheral surfaces $31_2$ formed at the inner periphery thereof. A projecting portion $12a3_2$ is formed at the bottom portion $12a2_2$ of the cup member $12a_2$. The boot mounting groove 32 is formed at an outer periphery of the cup member $12a_2$ on the opening side thereof. The bearing mounting surface 14 and the snap ring groove 15 are formed at the outer periphery of the shaft member 13a on the cup member $12a_2$ side, whereas the spline Sp is formed at the end portion on the opposite side to the cup member $12a_2$ side.

As illustrated in FIG. 24a and FIG. 24b, a joining end surface $50_2$ formed at the projecting portion $12a3_2$ of the bottom portion $12a2_2$ of the cup member $12a_2$ and the joining end surface 51 formed at the end portion of the shaft member 13a on the cup member $12a_2$ side are brought into abutment against each other, and are welded to each other by electron beam welding performed from the radially outer side. The welded portion 49 is formed of a bead formed by a beam radiated from the radially outer side of the cup member $12a_2$. Similarly to the outer joint member according to the first embodiment, the outer diameters B of the joining end surface $50_2$ and the joining end surface 51 are set to equal dimensions for each joint size. The welded portion 49 is formed on the joining end surface 51 located on the cup member $12a_2$ side with respect to the bearing mounting surface 14 of the shaft member 13a, and hence the bearing mounting surface 14 and the like can be processed in advance so that post-processing after welding can be omitted. Further, the electron beam welding does not cause formation of burrs at the welded portion. Thus, post-processing for the welded portion can also be omitted, thereby being capable of reducing the manufacturing cost.

The outer joint member $11_2$ is similar to the outer joint member described in the first embodiment in relation to the manufacturing method for the outer joint member 11 described above, and is similarly applicable to a second embodiment and a third embodiment of the present invention in relation to the manufacturing method for an outer joint member described above. Therefore, all of those are similarly applied, and redundant description is omitted.

Figure 25:
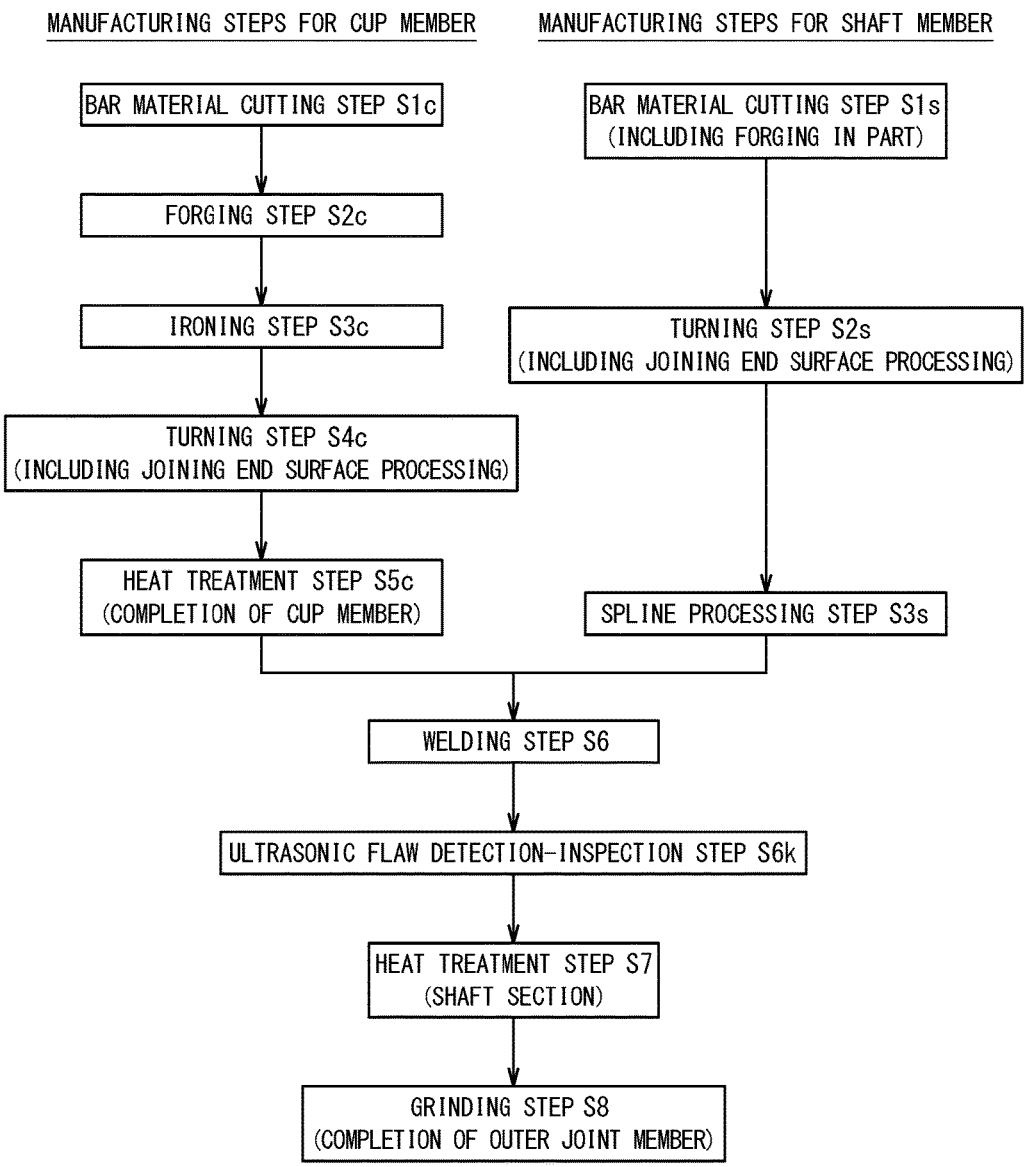
FIG. 25 is an illustration of an overview of a manufacturing method for an outer joint member according to a second embodiment of the present invention.

FIG. 25 is an illustration of a manufacturing method according to the second embodiment of the present invention. In the manufacturing steps of the second embodiment, the heat treatment step for the cup member, which is involved in the heat treatment step S7 in FIG. 3 as described in the first embodiment, is provided before the welding step S6 in the sequence and named "heat treatment step S5c", to thereby prepare the cup member as a finished product. Details of other aspects of the second embodiment than this aspect, that is, details of the overview of the respective steps, the states of the cup member and the shaft member in the main processing steps, the preparation of the cup member for common use, the welding method, the method for the ultrasonic flaw detection-inspection, the standardization of the product type, the configuration of the outer joint member, and the like as described above in connection with the manufacturing method according to the first embodiment are the same as those of the first embodiment. Therefore, all the details of the first embodiment are applied in the second embodiment, and only the difference is described.

As illustrated in FIG. 4b, the cup member 12a has a shape extending from the joining end surface 50 to the large-diameter cylindrical portion 12a1 via the bottom portion 12a2, and the portions to be subjected to heat treatment that involves quenching and tempering are the track grooves 30 and the cylindrical inner peripheral surface 42 located at the inner periphery of the cylindrical portion 12a1. Therefore, the cup member 12a generally has no risk of thermal effect on the heat-treated portion during the welding. For this reason, the cup member 12a is subjected to heat treatment before the welding to be prepared as a finished component. The manufacturing steps of the second embodiment are suitable in practical use.

In the manufacturing steps of the second embodiment, the cup member 12a is subjected to heat treatment for preparing the cup member 12a as a finished product, and is therefore assigned with a product number indicating a finished product for management. Thus, the standardization of the product type of the cup member 12a remarkably reduces the cost and alleviates the burden of production management. Further, the cup member 12a can be manufactured solely until the cup member 12a is completed as a finished product through the forging, turning, and heat treatment. Thus, the productivity is enhanced by virtue of reduction of setups and the like as well.

In the second embodiment, in FIG. 22 for illustrating the example of standardization of the product type of the cup member as described above in the first embodiment, only the product number of the cup member in FIG. 22 is changed to the product number indicating a finished product, whereas the product numbers of the shaft member and the outer joint member are the same as those of the first embodiment. Therefore, description thereof is omitted herein.

Figure 26:
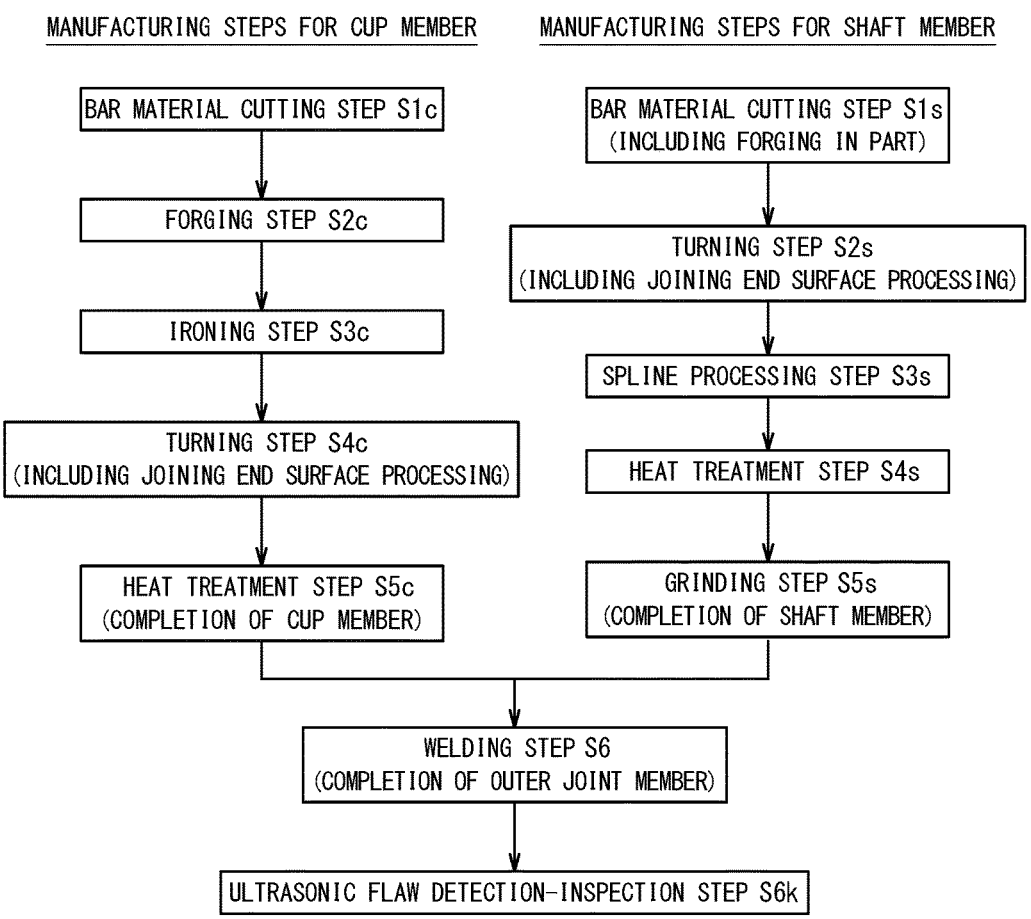
FIG. 26 is an illustration of an overview of a manufacturing method for an outer joint member according to a third embodiment of the present invention.

FIG. 26 is an illustration of a manufacturing method according to the third embodiment of the present invention. In the manufacturing steps of the third embodiment, the heat treatment steps for the cup section and the shaft section, which are involved in the heat treatment step S7 in FIG. 3 as described above in the first embodiment, and the grinding step S8 for the shaft section are provided before the welding step S6 in the sequence and named "heat treatment step S5c for cup member", "heat treatment step S4s for shaft member", and "grinding step S5s". Thus, both the cup member and the shaft member are prepared as finished products. Details of other aspects of the third embodiment than this aspect, that is, details of the overview of the respective steps, the states of the cup member and the shaft member in the main processing steps, the preparation of the cup member for common use, the welding method, the method for the ultrasonic flaw detection-inspection, the standardization of the product type, the configuration of the outer joint member, and the like as described above in connection with the manufacturing method according to the first embodiment are the same as those of the first embodiment. Therefore, all the details of the first embodiment are applied in the third embodiment, and only the difference is described.

After the spline processing step S3s, a hardened layer having a hardness of approximately from 50 HRC to 62 HRC is formed in a predetermined range of the outer peripheral surface of the shaft member by induction quenching in the heat treatment step S4s. Heat treatment is not performed on a predetermined portion in the axial direction, which includes the joining end surface 51. The heat treatment for the cup member, the assignment of the product number, and the like are the same as those in the manufacturing method according to the second embodiment, and redundant description is therefore omitted herein.

After the heat treatment step S4s, the shaft member is transferred to the grinding step S5s so that the bearing mounting surface 14 and the like are finished. Thus, the shaft member is obtained as a finished product. Then, the shaft member is assigned with a product number indicating a finished product for management. The manufacturing steps of the third embodiment are suitable in a case of a cup member and a shaft member having shapes and specifications with no risk of thermal effect on the heat-treated portion during the welding.

In the manufacturing steps of the third embodiment, both the cup member and the shaft member can be assigned with product numbers indicating finished products for management. Thus, the standardization of the product type of the cup member further remarkably reduces the cost and alleviates the burden of production management. Further, the cup member and the shaft member can be manufactured independently of each other until the cup member and the shaft member are completed as finished products through the forging, turning, heat treatment, grinding after heat treatment, and the like. Thus, the productivity is further enhanced by virtue of reduction of setups and the like as well.

In the third embodiment, in FIG. 16 for illustrating the example of standardization of the product type of the cup member as described above in the first embodiment, the product numbers of the cup member and the shaft member in FIG. 16 are changed to the product numbers indicating finished products. The product number of the outer joint member is the same as that of the first embodiment. Therefore, description thereof is omitted herein. Note that, the cup member and the shaft member to be prepared as finished components are not limited to the cup member and the shaft member subjected to finishing such as the above-mentioned grinding after heat treatment or cutting after quenching, but encompass a cup member and a shaft member in a state in which the heat treatment is completed while the finishing is uncompleted.

As described in the standardization of the product type, the cup member is not limited to one type for one joint size, that is, not limited to one type assigned with a single product number. Specifically, as described above, the cup member encompasses, for example, cup members of a plurality of types (assigned with a plurality of product numbers, respectively) that are prepared for one joint size based on different specifications of a maximum operating angle, and are also prepared so that the outer diameters B of the above-mentioned joining end surfaces of the cup members are set to equal dimensions. In addition, the cup member encompasses, for example, cup members of a plurality of types (assigned with a plurality of product numbers, respectively) that are prepared for one joint size in order to achieve management of the cup members in a plurality of forms including intermediate components before heat treatment and finished components in consideration of the joint function, the circumstances at the manufacturing site, the productivity, and the like, and are also prepared so that the outer diameters B of the above-mentioned joining end surfaces of the cup members are set to equal dimensions.

In the above-mentioned embodiments, the case to which electron beam welding is applied is described, but laser welding is also similarly applicable.

In the outer joint member according to the embodiments and described above, the cases where the present invention is applied to the double-offset type constant velocity universal joint as the plunging type constant velocity universal joint 10, and to the tripod type constant velocity universal joint as the plunging type constant velocity universal joint 10 are described. However, the present invention may be applied to an outer joint member of another plunging type constant velocity universal joint such as a cross-groove type constant velocity universal joint, and to an outer joint member of a fixed type constant velocity universal joint. Further, in the above, the present invention is applied to the outer joint member of the constant velocity universal joint, which is used to construct the drive shaft. However, the present invention may be applied to an outer joint member of a constant velocity universal joint, which is used to construct a propeller shaft.

The present invention is not limited to the above-mentioned embodiments. As a matter of course, various modifications can be made thereto without departing from the gist of the present invention. The scope of the present invention is defined in Claims, and encompasses equivalents described in Claims and all changes within the scope of claims.

DESCRIPTION OF REFERENCE SIGNS 1 drive shaft
2 intermediate shaft
3 spline
4 boot
5 boot
6 support bearing
10 plunging type constant velocity universal joint
11 outer joint member
11' workpiece
12 cup section
12a cup member
12a1 cylindrical portion
12a2 bottom portion
13 long shaft section
13a shaft member
14 bearing mounting surface
16 inner joint member
17 tripod member
19 torque transmitting element (roller)
20 fixed type constant velocity universal joint
21 outer joint member
22 inner joint member
23 torque transmitting element (ball)

24 cage
30 track groove
31 inner peripheral surface
40 track groove
41 torque transmitting element (ball)
42 cylindrical inner peripheral surface
49 welded portion
50 joining end surface
51 joining end surface
100 welding apparatus
101 electron gun
108 case
109 vacuum pump
111 sealed space
120 ultrasonic flaw detection-inspection apparatus
121 base
122 water bath
123 workpiece support
124 upper center hole guide
125 rotary drive device
126 lower center hole guide
128 drive positioning device
129 vertical-direction drive positioning device
130 horizontal-direction drive positioning device
142 drive cylinder
143 rotary support member
145 servomotor
156 drive cylinder
160 probe
161 drive positioning device
165 drive cylinder
166 drive cylinder
167 arm member
168 gear
169 electric rotary actuator
170 gear
171 rack
B1 outer diameter
B2 outer diameter
D inner diameter
E inner diameter
G transmission pulse
Gr1 reflection echo
Gr2 reflection echo
Gr3 reflection echo
K defect
O joint center
O1 curvature center
O2 curvature center
RC circumferential inclination angle (incident angle)
RC' refraction angle
RL1 axial inclination angle (incident angle)
RL1' refraction angle
RL2 axial inclination angle (incident angle)
RL2' refraction angle
X1 threshold value
X2 threshold value

The invention claimed is:

1. A manufacturing method for an outer joint member of a constant velocity universal joint,
the outer joint member comprising:
a cup section having track grooves formed in an inner periphery of the cup section, which are engageable with torque transmitting elements; and
a shaft section formed at a bottom portion of the cup section,
the outer joint member being constructed by forming the cup section and the shaft section as separate members, and by welding a cup member forming the cup section and a shaft member forming the shaft section to each other,
the manufacturing method at least comprising:
a welding step of welding the cup member and the shaft member to form a workpiece by irradiating a beam to joining end portions of the cup member and the shaft member; and
an ultrasonic flaw detection-inspection step of inspecting a welded portion formed in the welding step by a plurality of ultrasonic flaw detection methods with one shared probe, wherein
the plurality of ultrasonic flaw detection methods comprise a circumferential angle beam flaw detection method and an axial angle beam flaw detection method,
the circumferential angle beam flaw detection method includes a plurality of steps each of which comprises positioning the one shared probe in an X-axis direction that is perpendicular to a predetermined diameter line in a cross section of the workpiece perpendicular to an axis of the workpiece, in a Y-axis direction that is parallel to the predetermined diameter line and in a Z-axis direction that is parallel to the axis of the workpiece while making an axis of an ultrasonic transmission pulse to be transmitted from the one shared probe perpendicular to the predetermined diameter line and offset in the Y-axis direction with respect to a longitudinal section of the workpiece including the axis of the workpiece, transmitting the ultrasonic transmission pulse from the one shared probe to the workpiece, and receiving a reflection echo from the workpiece,
wherein, in the plurality of steps of the circumferential angle beam flaw detection method, a position of the one shared probe in the Z-axis direction is different in each of the plurality of steps, and a position of the one shared probe in the X-axis direction and a position of the one shared probe in the Y-axis direction are the same in each of the plurality of steps, and
the axial angle beam flaw detection method includes a plurality of steps each of which comprises positioning the one shared probe in the X-axis direction, in the Y-axis direction and in the Z-axis direction while making the axis of the ultrasonic transmission pulse have an axial inclination angle with respect to the cross section of the workpiece, transmitting the ultrasonic transmission pulse from the one shared probe to the workpiece, and receiving a reflection echo from the workpiece,
wherein, in the plurality of steps of the axial angle beam flaw detection method, a position of the one shared probe in the Z-axis direction is different in each of the plurality of steps, and a position of the one shared probe in the X-axis direction and a position of the one shared probe in the Y-axis direction are the same in each of the plurality of steps.

2. The manufacturing method for an outer joint member of a constant velocity universal joint according to claim 1, wherein the positioning of the one shared probe is controlled by a program.

3. The manufacturing method for an outer joint member of a constant velocity universal joint according to claim 1, wherein the ultrasonic flaw detection-inspection step further comprises rotating the workpiece during the inspecting.

4. The manufacturing method for an outer joint member of a constant velocity universal joint according to claim 1, wherein the axial angle beam flaw detection method further includes repeating the plurality of steps a plurality times, and changing the axial inclination angle each of the plurality of times the plurality of steps is performed.

5. An ultrasonic flaw detection-inspection method for a welded portion of an outer joint member of a constant velocity universal joint, the outer joint member comprising:
- a cup section having track grooves formed in an inner periphery of the cup section, which are engageable with torque transmitting elements; and
- a shaft section formed at a bottom portion of the cup section, the outer joint member being constructed by forming the cup section and the shaft section as separate members, and by welding a cup member forming the cup section and a shaft member forming the shaft section to each other to form a workpiece, the ultrasonic flaw detection-inspection method comprising inspecting the welded portion by a plurality of ultrasonic flaw detection methods with one shared probe wherein the plurality of ultrasonic flaw detection methods comprise a circumferential angle beam flaw detection method and an axial angle beam flaw detection method, the circumferential angle beam flaw detection method includes a plurality of steps each of which comprises positioning the one shared probe in an X-axis direction that is perpendicular to a predetermined diameter line in a cross section of the workpiece perpendicular to an axis of the workpiece, in a Y-axis direction that is parallel to the predetermined diameter line and in a Z-axis direction that is parallel to the axis of the workpiece while making an axis of an ultrasonic transmission pulse to be transmitted from the one shared probe perpendicular to the predetermined diameter line and offset in the Y-axis direction with respect to a longitudinal section of the workpiece including the axis of the workpiece, transmitting the ultrasonic transmission pulse from the one shared probe to the workpiece, and receiving a reflection echo from the workpiece, wherein, in the plurality of steps of the circumferential angle beam flaw detection method, a position of the one shared probe in the Z-axis direction is different in each of the plurality of steps, and a position of the one shared probe in the X-axis direction and a position of the one shared probe in the Y-axis direction are the same in each of the plurality of steps, and the axial angle beam flaw detection method includes a plurality of steps each of which comprises positioning the one shared probe in the X-axis direction, in the Y-axis direction and in the Z-axis direction while making the axis of the ultrasonic transmission pulse have an axial inclination angle with respect to the cross section of the workpiece, transmitting the ultrasonic transmission pulse from the one shared probe to the workpiece, and receiving a reflection echo from the workpiece, wherein, in the plurality of steps of the axial angle beam flaw detection method, a position of the one shared probe in the Z-axis direction is different in each of the plurality of steps, and a position of the one shared probe in the X-axis direction and a position of the one shared probe in the Y-axis direction are the same in each of the plurality of steps.

6. The ultrasonic flaw detection-inspection method for a welded portion of an outer joint member of a constant velocity universal joint according to claim 5, wherein the axial angle beam flaw detection method further includes repeating the plurality of steps a plurality times, and changing the axial inclination angle each of the plurality of times the plurality of steps is performed.

7. The ultrasonic flaw detection-inspection method for a welded portion of an outer joint member of a constant velocity universal joint according to claim 5, wherein the ultrasonic flaw detection-inspection step further comprises rotating the workpiece during the inspecting.

\* \* \* \* \*